United States Patent
Edlund et al.

[11] Patent Number: 5,997,594
[45] Date of Patent: Dec. 7, 1999

[54] STEAM REFORMER WITH INTERNAL HYDROGEN PURIFICATION

[75] Inventors: David J. Edlund, Bend; William A. Pledger, Sisters, both of Oreg.

[73] Assignee: Northwest Power Systems, LLC, Bend, Oreg.

[21] Appl. No.: 08/951,091

[22] Filed: Oct. 15, 1997

Related U.S. Application Data

[63] Continuation-in-part of application No. 08/741,057, Oct. 30, 1996, Pat. No. 5,861,137.

[51] Int. Cl.$^6$ ........................................... C10J 3/68
[52] U.S. Cl. .................. 48/76; 48/127.7; 48/63; 422/217; 422/218; 95/56; 96/7; 96/11
[58] Field of Search ............... 48/76, 127.7, 63; 422/217, 218; 423/652, 655; 95/56; 96/7, 11

[56] References Cited

U.S. PATENT DOCUMENTS

| | | |
|---|---|---|
| 3,849,076 | 11/1974 | Gryaznov et al. . |
| 4,132,668 | 1/1979 | Gryaznov et al. . |
| 4,197,152 | 4/1980 | Palty et al. . |
| 4,329,157 | 5/1982 | Dobo et al. . |
| 4,650,814 | 3/1987 | Keller ........................................ 518/703 |
| 4,654,063 | 3/1987 | Auvil et al. . |
| 4,684,581 | 8/1987 | Struthers . |
| 4,713,234 | 12/1987 | Weirich et al. . |
| 4,810,485 | 3/1989 | Marianowski et al. . |
| 5,326,550 | 7/1994 | Adris et al. . |
| 5,354,547 | 10/1994 | Rao et al. . |
| 5,393,325 | 2/1995 | Edlund ........................................ 95/56 |
| 5,449,848 | 9/1995 | Itoh ........................................ 585/430 |
| 5,498,278 | 3/1996 | Edlund ........................................ 96/11 |
| 5,509,942 | 4/1996 | Dodge . |
| 5,525,322 | 6/1996 | Willms . |
| 5,612,012 | 3/1997 | Soma et al. . |
| 5,637,259 | 6/1997 | Galuszka et al. . |
| 5,639,431 | 6/1997 | Shirasaki et al. . |
| 5,645,626 | 7/1997 | Edlund et al. ........................... 95/56 |
| 5,658,681 | 8/1997 | Sato et al. . |
| 5,705,916 | 1/1998 | Rudbeck et al. . |
| 5,734,092 | 3/1998 | Wang et al. ........................... 73/23.25 |
| 5,782,960 | 7/1998 | Ogawa et al. ........................... 96/11 |
| 5,814,112 | 9/1998 | Elliot et al. ........................... 48/197 |

OTHER PUBLICATIONS

Adris, A. M., et al., "A Fluidized Bed Membrane Reactor for the Steam Reforming of Methane," The Canadian Journal of Chemical Engineering, vol. 69, pp. 1061–1070, (Oct., 1991).

Amphlett, J.C., et al., "On Board Hydrogen Purification for Steam Reformer/PEM Fuel Cell Vehicle Power Plants," Energy Progress X, Proceedings of the 10$^{th}$ World Hydrogen Energy Conference, Cocoa Beach, Florida, U.S.A., vol. 3, pp. 1681–1690 (Jun., 1994).

Chai, M., et al., "Promotion of Methane Steam Reforming Using Ruthenium–Dispersed Microporous Alumina Membrane Reactor," Chemistry Letters, The Chemical Society of Japan, pp. 41–44 (1993).

(List continued on next page.)

Primary Examiner—Nina Bhat
Attorney, Agent, or Firm—Kolisch, Hartwell, Dickinson, McCormack & Heuser

[57] ABSTRACT

A steam reformer with internal hydrogen purification includes internal bulk hydrogen purification, internal hydrogen polishing to remove trace levels of carbon monoxide and carbon dioxide, an integrated combustion method utilizing waste gas to heat the reformer, efficient integration of heat transfer, and a compact design. One steam reformer shown includes a concentric cylindrical architecture nesting an annular combustion region, an annular reforming region, an annular hydrogen transport region, and a cylindrical polishing region. Other reformers shown include modified combustion systems distributed within a reformation region, isolated vaporization chambers, combustion systems providing uniform temperature gradient, and plate membrane construction methods.

37 Claims, 12 Drawing Sheets

OTHER PUBLICATIONS

"Compact, Lightweight Fuel Reformer for Fuel Cells," Argonne National Laboratory/U.S. Department of Energy (Jul., 1996).

Edlund, David J. and William A. Pledger, "The Practical Use of Metal–Membrane Reactors for Industrial Applications," The 1995 Membrane Technology Reviews, pp. 89–97 (Nov., 1994).

Knapton, A.G., "Palladium Alloys for Hydrogen Diffusion Membranes," Platinum Metals Review, vol. 21, 44–50 (1977).

Minet, R. G., et al., "Experimental Studies of A Ceramic Membrane Reactor for the Steam/Methane Reaction at Moderate Temperatures (400–700° C)," Symposium on Natural Gas Upgrading II Presented before The Division of Petroleum Chemistry, Inc., Meeting of American Chemical Society, San Francisco, California, U.S.A., pp. 245–248 (Apr., 1992).

Oertel, Michael, et al., "Steam Reforming of Natural Gas with Integrated Hydrogen Separation for Hydorogen Production," Chemical Engineering Technology, vol. 10, pp. 248–255 (1987).

Shu, J., et al., "Catalytic Palladium–Based Membrane Reactors: A Review," The Canadian Journal of Chemical Engineering, vol. 69, pp. 1036–1060 (Oct., 1991).

Teagan, W.P., et al., "Cost Reduction of Fuel Cells for Transportation Applications—Fuel Processing Options," Fifth Grove Fuel Cell Symposium, Commonwealth Institute, London, U.K. (Sep. 22–25, 1997).

Edlund, Dr. David and William Pledger, "Development of a Compact and Economical Steam Reformer for Fuel–Cell Systems," Fifth Grove Fuel Cell Symposium, Commonwealth Instutute, London, U.K., p. 6 (Sep. 22–25, 1997).

Amphlett, J. C., et al., "Simulation of a 250 kW Diesel Fuel Processor/PEM Fuel Cell System," Fifth Grove Fuel Cell Symposium, Commonwealth Institute, London, U.K., p. 8 (Sep. 22–25, 1997).

Ledjeff–Hey, K., et al., "Compact Hydrogen Production Systems for Solid Polymer Fuel Cells," Fifth Grove Fuel Cell Symposium, Commonwealth Institute, London, U.K., p. 17 (Sep. 22–25, 1997).

Emonts, B., et al., "Compact Methanol Reformer Test for Fuel–Cell Powered Light–Duty Vehicles," Fifth Grove Fuel Cell Symposium, Commonwealth Institute, London, U.K., p. 42 (Sep. 22–25, 1997).

Emonts, B., et al., "Compact Methanol Reformer Test for Fuel–Cell Powered Light–Duty Vehicles," Fifth Grove Fuel Cell Symposium, Commonwealth Institute, London, U.K., (no page No.), (Sep. 22–25, 1997).

Menzer, R., et al., "Fuel Processing in Fuel Cell Systems for Mobile Applications—Gasoline as Energy Carrier On–Bord," Fifth Grove Fuel Cell Symposium, Commonwealth Institute, London, U.K., (no page No.), (Sep. 22–25, 1997).

Jørgensen, S. Lægsgaard, et al., "Application of Pd–Membranes for the Production of Pure Hydrogen in Methanol–Based Fuel Cell Powered Vehicles," Proceedings of Fourth Workshop: Optimisation of Catalytic Membrane Reactor Systems, ESF Network, Catalytic Membrane Reactors, Oslo, Norway, pp. 51–57 (May 30–31, 1997).

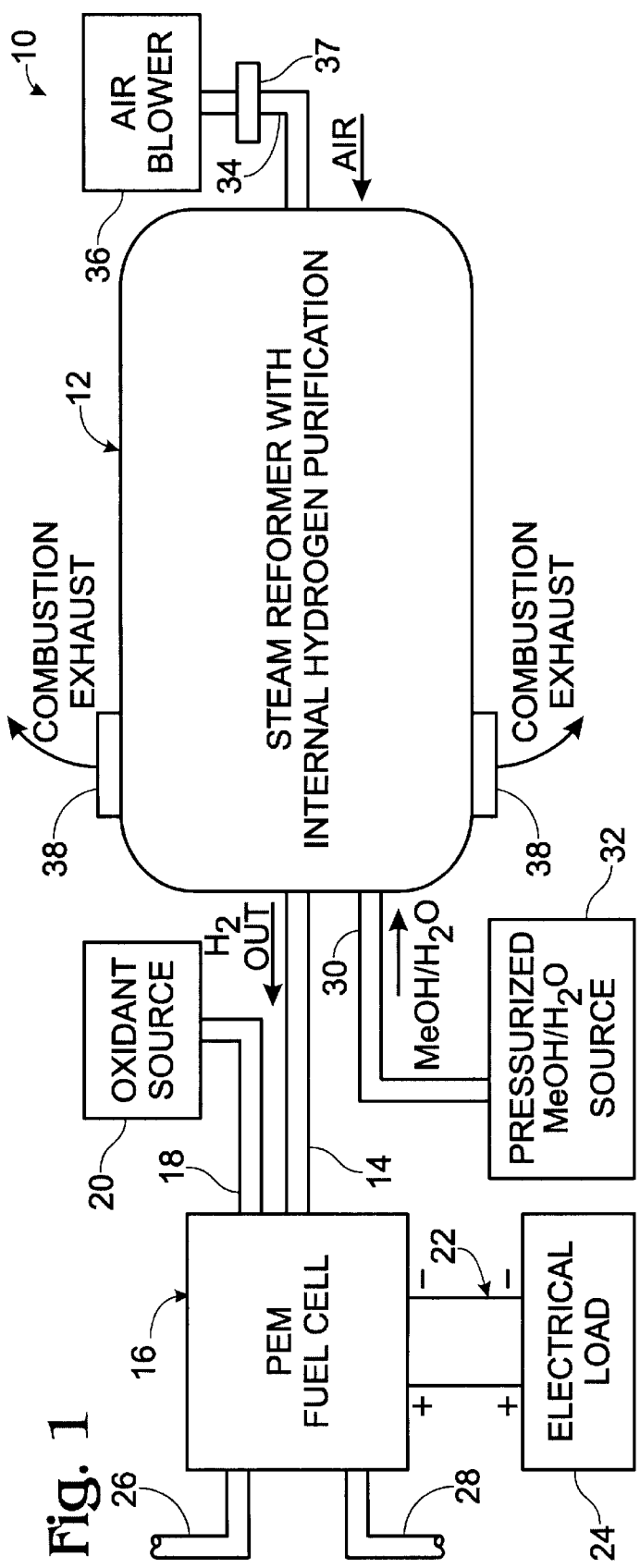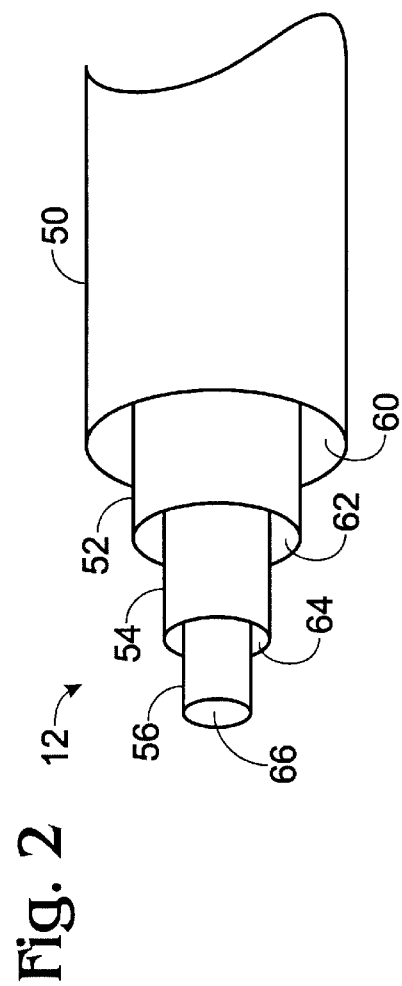
Fig. 1
Fig. 2

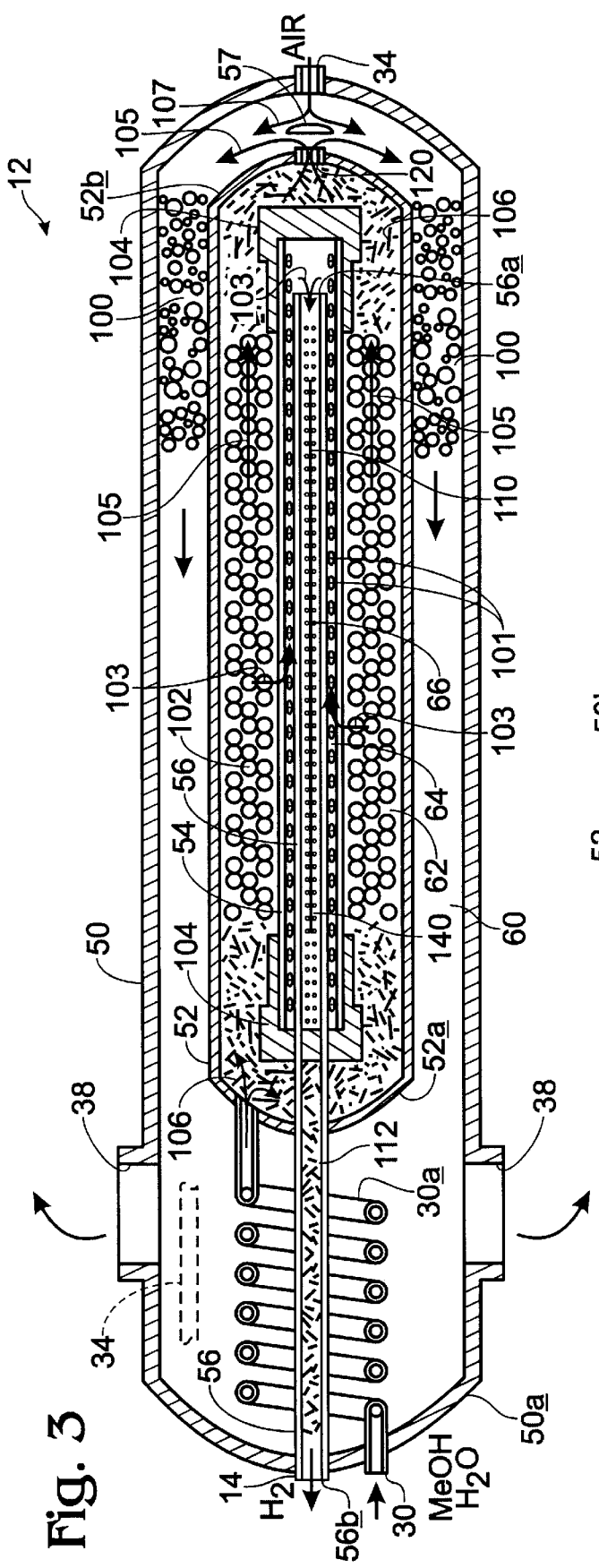
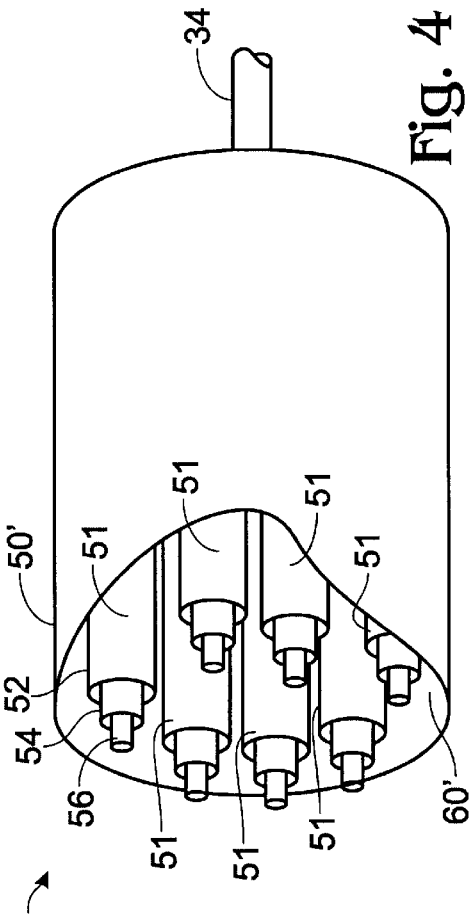
Fig. 3
Fig. 4

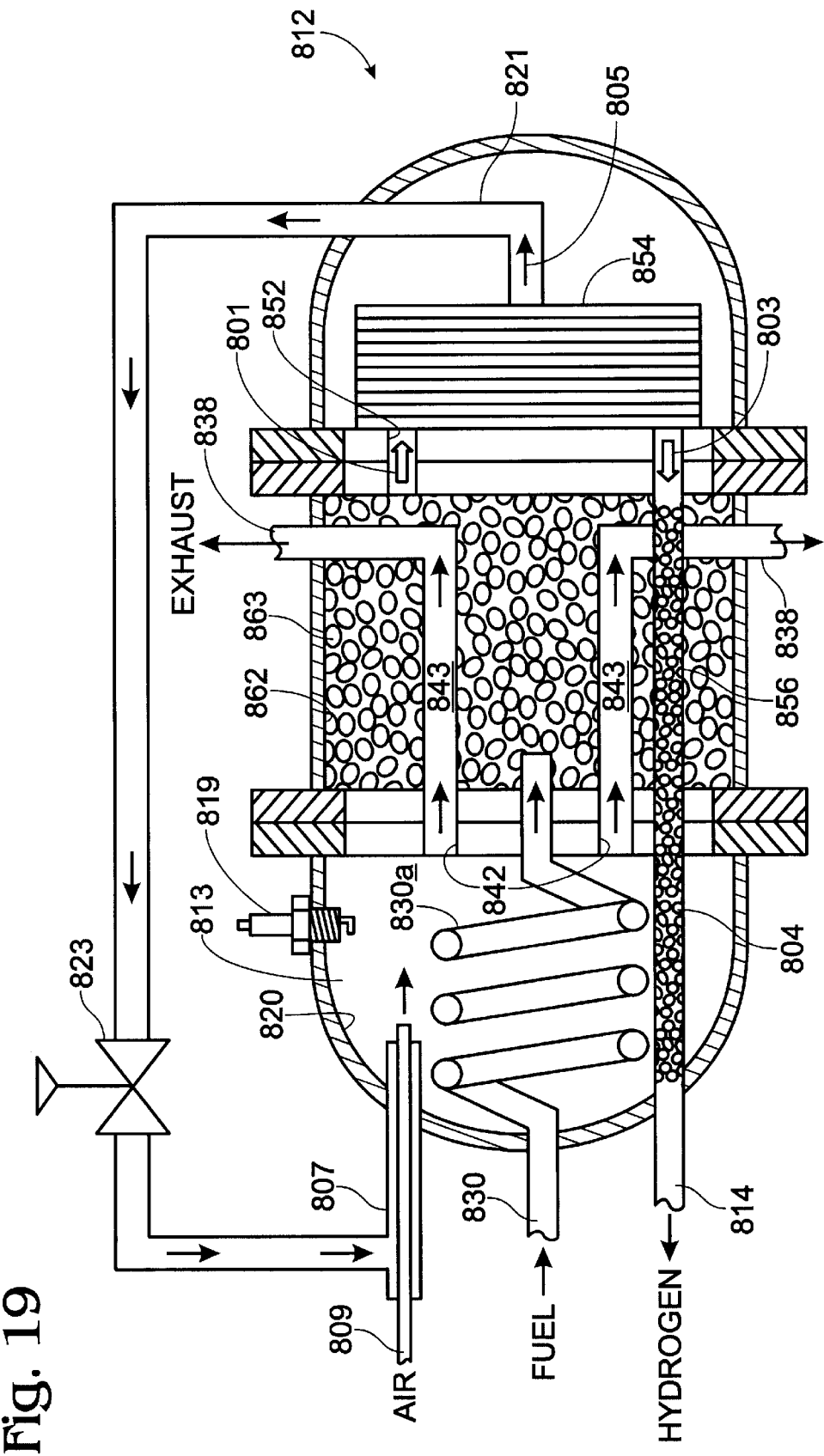

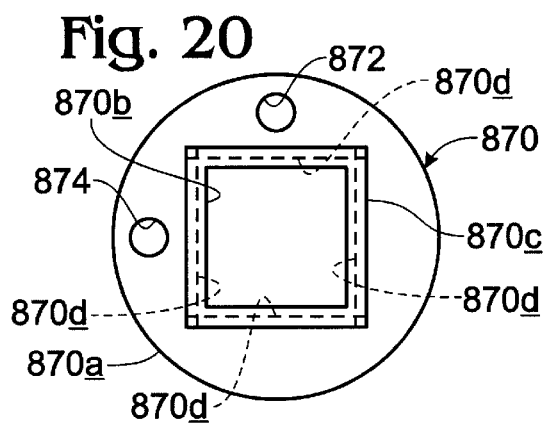
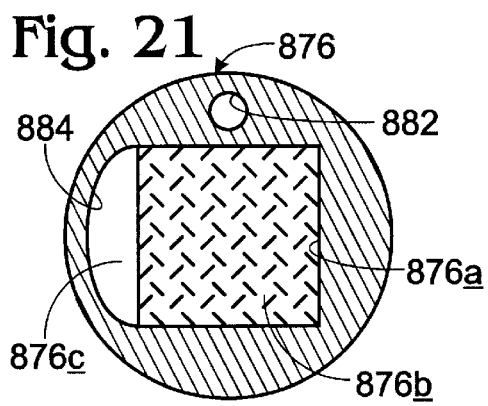
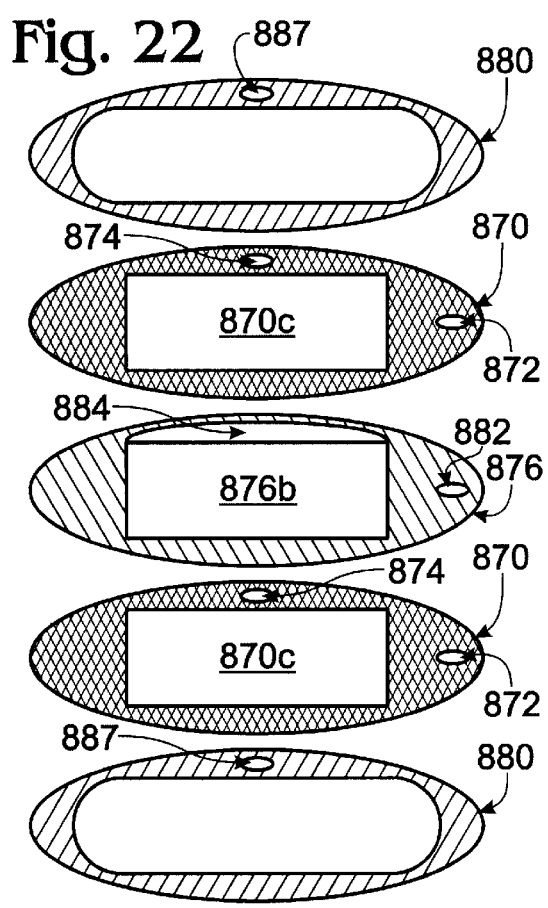
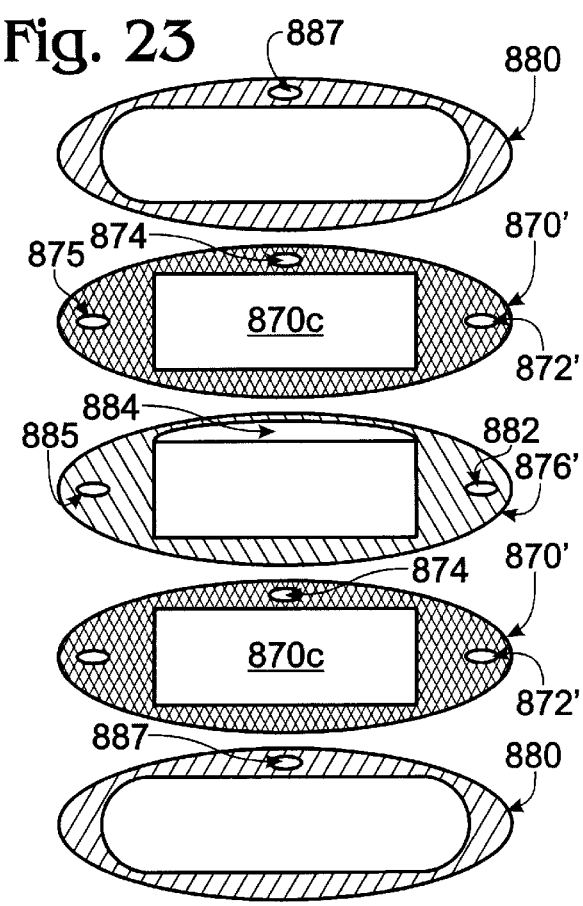
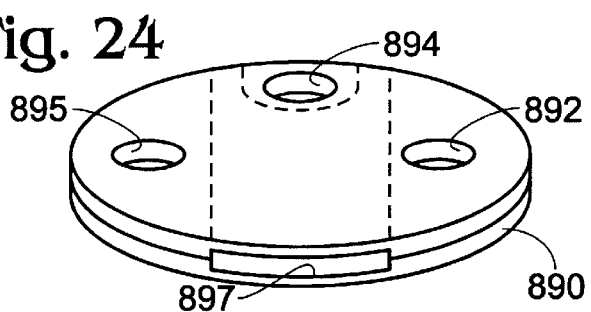

STEAM REFORMER WITH INTERNAL HYDROGEN PURIFICATION

RELATED APPLICATION

The present application is a continuation-in-part of prior U.S. patent application Ser. No. 08/741,057 filed Oct. 30, 1996 U.S. Pat. No. 5,861,137 and entitled Steam Reformer With Internal Hydrogen Purification.

BACKGROUND OF THE INVENTION

The present invention relates generally to energy conversion, and particularly to a process and apparatus for production of purified hydrogen by steam reforming.

Purified hydrogen is an important fuel source for many energy conversion devices. For example, fuel cells use purified hydrogen and an oxidant to produce an electrical potential. A process known as steam reforming produces by chemical reaction hydrogen and certain byproducts or impurities. A subsequent purification process removes the undesirable impurities to provide hydrogen sufficiently purified for application to a fuel cell.

Under steam reforming, one reacts steam and alcohol, (methanol or ethanol) or a hydrocarbon (such as methane or gasoline or propane), over a catalyst. Steam reforming requires elevated temperature, e.g., between 250 degrees centigrade and 800 degrees centigrade, and produces primarily hydrogen and carbon dioxide. Some trace quantities of unreacted reactants and trace quantities of byproducts such as carbon monoxide also result from steam reforming.

Trace quantities of carbon monoxide, certain concentrations of carbon dioxide, and in some cases unsaturated hydrocarbons and alcohols will poison a fuel cell. Carbon monoxide adsorbs onto the platinum catalyst of the fuel cell and inhibits operation of the fuel cell, i.e., reduces the power output of the fuel cell. To a lesser degree, carbon dioxide and other unsaturated hydrocarbons and alcohols have the same result. All impurities to some extent reduce by dilution the partial pressure of hydrogen in the fuel cell and increase the mass transfer resistance for hydrogen to diffuse to the platinum catalyst, and thereby reduce power output of the fuel cell. Thus, fuel cells require an appropriate fuel input, i.e., purified hydrogen with no additional elements contributing to a loss in fuel cell efficiency.

Traditionally, hydrogen purification attempts to always maximize harvest of hydrogen from the reforming process. To maximize the amount of hydrogen obtained, a relatively expensive device, e.g., a thick and high quality palladium membrane, serves as a hydrogen-permeable and hydrogen-selective membrane [Ledjeff-Hey, K., V. Formanski, Th. Kalk, and J. Roes, "Compact Hydrogen Production Systems for Solid Polymer Fuel Cells" presented at the Fifth Grove Fuel Cell Symposium, Sep. 22–25, 1997]. Such thick, high quality palladium alloy membranes support maximum harvest of hydrogen with minimal, i.e., acceptable, impurities for use in a fuel cell. Such high level of purification, however, requires significant investment in the thick, high quality palladium membrane.

Traditionally, the process of steam reforming and the subsequent process of hydrogen purification occur in separate apparatus. The advantages of combining steam reforming and hydrogen purification in a single device are known [Oertel, M., et al, "Steam Reforming of Natural Gas with Integrated Hydrogen Separation for Hydrogen Production", Chem. Eng. Technol 10 (1987) 248–255; Marianowski, L. G., and D. K. Fleming, "Hydrogen Forming Reaction Process" U.S. Pat. No. 4,810,485, Mar. 7, 1989]. An integrated steam reforming and hydrogen purification device should provide a more compact device operating at lower temperatures not limited by the normal equilibrium limitations. Unfortunately, such a device has yet to be reduced to practical design. Where theory in this art recognizes the advantage of combining steam reformation and hydrogen purification in a single device, the art has yet to present a practical, i.e., economical, design.

Thus, a practical integrated steam reforming and hydrogen purification device has not yet become available. The subject matter of the present invention provides a practical combined steam reforming and hydrogen purification device.

SUMMARY OF THE INVENTION

A process for producing hydrogen containing concentrations of carbon monoxide and carbon dioxide below a given level begins by reacting an alcohol vapor (such as methanol) or a hydrocarbon vapor (such as propane) and steam to produce product hydrogen, carbon monoxide, and carbon dioxide. The reacting step occurs in the vicinity of, or immediately preceding, a hydrogen-permeable and hydrogen-selective membrane and the product hydrogen permeates the membrane. Since the membrane is likely to have holes and other defects, concentrations of the carbon monoxide and carbon dioxide above said given level also pass through the membrane. A methanation catalyst bed lies at the permeate side of the membrane and is heated whereby carbon monoxide and carbon dioxide in the methanation catalyst bed convert to methane and yield a product hydrogen stream with concentrations of carbon monoxide and carbon dioxide below said given level. Optionally, reforming catalyst may also lie at the permeate side of the membrane along with the methanation catalyst to convert to product hydrogen any unreacted alcohol or hydrocarbon feed that passes through holes or other defects in the membrane. The process concludes by withdrawing the product hydrogen from the methanation catalyst bed.

A steam reformer under the present invention includes a tubular or planar hydrogen-permeable and hydrogen selective membrane or immediately precedes the membrane. A reforming bed surrounds at least part of the membrane. An inlet to the reforming bed receives a mixture of alcohol or hydrocarbon vapor and steam and an outlet from the reforming bed releases reforming byproduct gasses. A heating element heats the reforming bed to an operating temperature and a second bed including a methanation catalyst is placed at the permeate side of the membrane. A reformer outlet withdraws hydrogen gas from the second bed. According to one aspect of the present invention, the heating element is a third bed including an oxidation catalyst surrounding at least a portion of the first bed. The reforming byproduct gasses released from the reforming bed mix with an air source and catalytically ignite to generate heat and thermally support the process of reforming within the reforming bed. In accordance with another aspect of the present invention, the reformer receives a liquid alcohol or hydrocarbon and liquid water feed and vaporizes the alcohol or hydrocarbon and water by use of heat generated in the oxidation catalyst bed. Under the present invention, fuels applied to the oxidation catalyst bed include a selected amount of hydrogen allowed into the reforming byproduct gasses to support the reforming process without requiring an additional fuel source.

The subject matter of the present invention is particularly pointed out and distinctly claimed in the concluding portion of this specification. However, both the organization and method of operation of the invention, together with further advantages and objects thereof, may best be understood by reference to the following description taken with the accompanying drawings wherein like reference characters refer to like elements.

BRIEF DESCRIPTION OF THE DRAWINGS

For a better understanding of the invention, and to show how the same may be carried into effect, reference will now be made, by way of example, to the accompanying drawings in which:

FIG. 1 illustrates generally an energy conversion system including a fuel cell and a steam reformer with internal hydrogen purification according to one form of the present invention.

FIG. 2 illustrates schematically a concentric, cylindrical architecture for the steam reformer with internal hydrogen purification of FIG. 1.

FIG. 3 illustrates in cross section the steam reformer with internal hydrogen purification of FIG. 1.

FIG. 4 illustrates schematically an alternate architecture for the steam reformer under the present invention nesting multiple reformer tubes within a common combustion region.

FIG. 19 illustrates the steam reformer of FIG. 18 in section.

FIGS. 20 and 21 show components of the membrane module for the steam reformer of FIGS. 18 and 19.

FIG. 22 illustrates a component stack for the membrane module of the steam reformer of FIGS. 18 and 19 providing a series feed gas flow arrangement.

FIG. 23 illustrates a component stack for the membrane module of the steam reformer of FIGS. 18 and 19 providing a parallel feed gas flow arrangement.

FIG. 24 illustrates a component stack for the membrane module of the steam reformer of FIGS. 18 and 19 incorporating an exhaust plate for internal heating of the membrane module.

DETAILED DESCRIPTION OF THE PREFERRED EMBODIMENT

Figure 5:
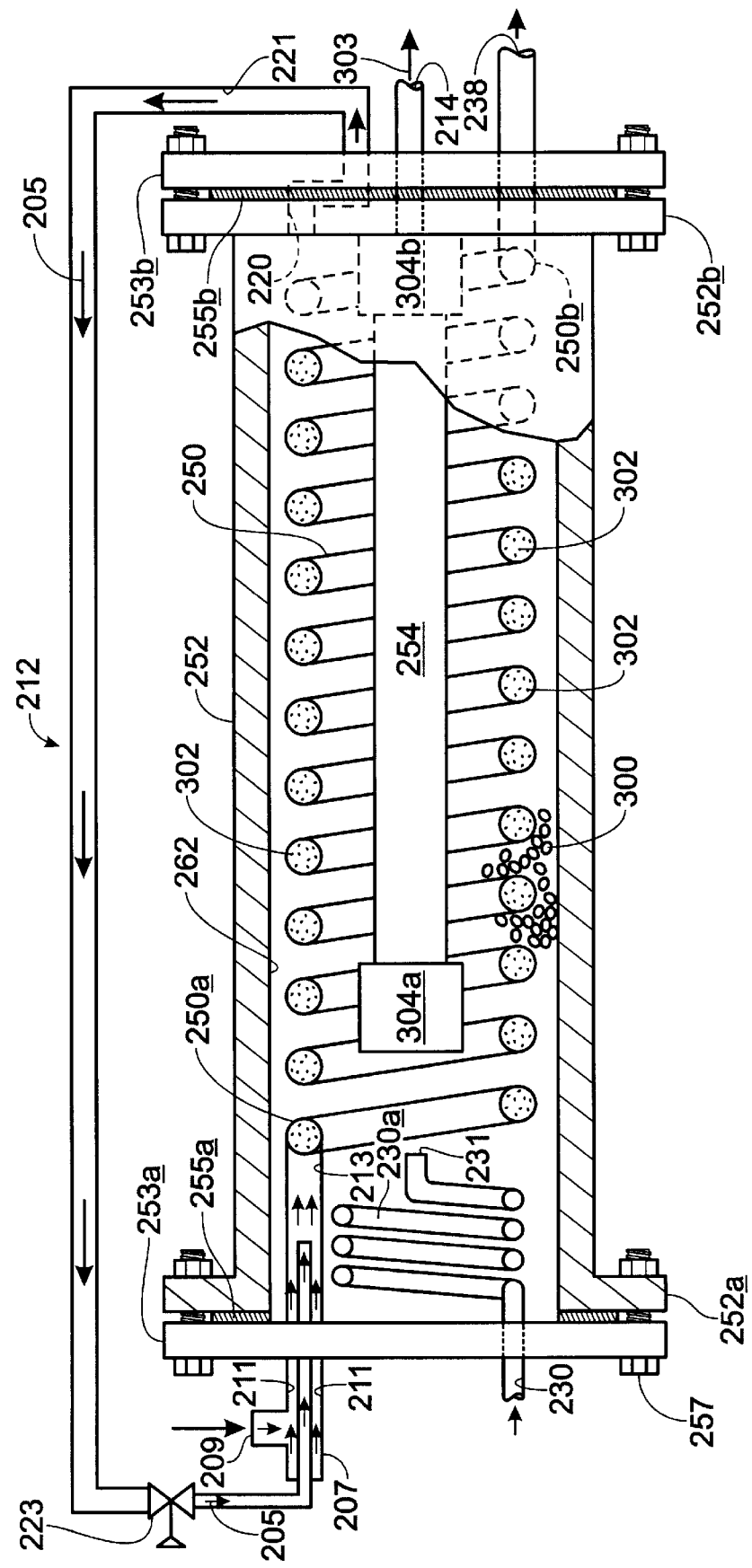
FIG. 5 illustrates schematically and partially in cross section a steam reformer with internal hydrogen purification according to the present invention including a modified combustion system distributed within the reformation region.

FIG. 1 shows an energy conversion system 10 employing a steam reformer with internal hydrogen purification (reformer) 12 according to a preferred form of the present invention. Reformer 12 provides at its outlet 14 purified hydrogen to a PEM fuel cell 16. Fuel cell 16 receives at its inlet 18 an oxidant from oxidant source 20. Fuel cell 16 produces an electrical potential 22 for application to an electrical load 24, e.g., an electrical motor. Fuel cell 16 also includes outlets 26 and 28 serving as fuel and oxidant outlets, respectively.

For purposes of describing operation of reformer 12, the liquid feedstock will be methanol (MeOH) and water, although other alcohols or hydrocarbons may be used in place of methanol. Reformer 12 receives at its fuel inlet 30 pressurized liquid methanol and water from a pressurized methanol/water source 32. As described more fully hereafter, the pressurized mix of liquid methanol and water vaporizes within reformer 12 and reacts with a reforming catalyst to produce a hydrogen stream and a byproduct stream. A hydrogen-selective membrane separates the hydrogen stream from the byproduct stream. The hydrogen stream passes, by pressure differential, through the membrane and subsequently through a polishing catalyst to appear at the outlet 14 of reformer 12.

While traditional reforming technology allows a high percentage of hydrogen produced to be taken across a selective membrane, the process and apparatus of the present invention takes less than a maximum available amount of hydrogen across the selective membrane. The present invention thereby allows use of a lesser-grade and, therefore, less expensive selective membrane. In addition, because less than the maximum amount of hydrogen is separated as a product stream, the required membrane area is reduced under this aspect of the present invention. The remaining portion of hydrogen enters the byproduct stream, mixes with air provided at inlet 34 by air blower 36, and reacts with a combustion catalyst within reformer 12 to support elevated temperatures needed for steam reforming within reformer 12. Reformer 12 thereby uses the byproduct stream, including a selected amount of hydrogen remaining therein, as a fuel source for its combustion process. No additional fuel source is applied to reformer 12 to support combustion. Reformer 12 also includes a plurality of combustion exhaust ports 38 releasing combustion byproducts.

The optimum amount of hydrogen to recover as a product stream is calculated from the heating value (enthalpy of combustion) of hydrogen. Sufficient hydrogen must be supplied in the byproduct stream to the catalytic combustion region so that the heat of combustion exceeds the total heat requirement of the reformer. The total heat requirement of the reformer ($\Delta H_{total}$) is given by $$\Delta H_{total} = \Delta H_{rxn} + \Delta H_{vap} + \Delta H_{cp} + \Delta H_{loss}$$

where $\Delta H_{rxn}$ is the enthalpy of the reforming reactions; $\Delta H_{vap}$ is the enthalpy of vaporization of the liquid feed stock; $\Delta H_{cp}$ is the enthalpy required to heat the vaporized feed stock to the reforming temperature; and $\Delta H_{loss}$ is the heat lost to the surrounding environment. Heat loss from the reformer is minimized (and reduced to a negligible degree) with adequate insulation.

In the case of steam reforming methanol according to the following reaction stoichiometry $$CH_3OH + H_2O = CO_2 + 3H_2$$

where 8.4 gmole methanol and 8.4 gmole water are required to yield sufficient hydrogen (21 std. ft³) to generate about 1 kW$_e$. Assuming no heat loss and no heat exchange (between discharged hot streams and the relatively cold feed stock stream) $\Delta H_{total}$ is 300 kcal. Since the heat of combustion for hydrogen is 57.8 kcal/gmole, approximately 5.2 gmoles of hydrogen (4.3 std.ft³) must be combusted to provide the required 300 kcal of heat for steam reforming sufficient methanol to generate 1 kW$_e$. So, 70% to 80% of the hydrogen produced in the reformer is recovered as a product stream and the remaining 20% to 30% of the hydrogen is passed to the catalytic combustor in the byproduct stream to provide a fuel stream with sufficient heating value to meet the heating requirements ($\Delta H_{total}$) of the reformer.

FIG. 2 illustrates schematically the concentric cylindrical architecture of steam reformer 12. In FIG. 2, reformer 12 includes in concentric relation an outermost metal tube 50, an inner metal tube 52, a hydrogen-selective membrane tube 54, and an innermost metal tube 56. Tubes 50, 52, 54, and 56 are of successively smaller diameter and arranged in concentric relation to one another. An annular combustion region 60 exists in the space within tube 50 but external of tube 52. An annular reforming region 62 exists within tube 52 but external of membrane tube 54. An annular hydrogen transport region 64 exists within membrane tube 54, but external of tube 56. A cylindrical polishing region 66 resides within the metal tube 56.

FIG. 3 illustrates in cross section the steam reformer 12. In FIG. 3, outermost metal tube 50, a generally closed-end tubular structure, receives at one end via inlet 34 an air supply and releases at combustion ports 38 combustion byproducts. Within combustion region 60, a combustion catalyst 100 resides near air inlet 34. Alternatively, combustion catalyst 100 may be arranged as a plurality of bands spaced at intervals within combustion region 60. Suitable combustion catalyst materials include platinum supported on alumina or other inert and thermally-stable ceramic. Inlet 30, carrying the pressurized mix of methanol and water, passes through the end wall 50a of tube 50 and forms a coil 30a wrapping about the innermost metal tube 56 within the combustion region 60, although metal tube 56 need not necessarily pass through the axis of coil 30a. The distal end of coil 30a passes through the closed end 52a of tube 52 and opens into the reforming region 62. The pressurized mix of liquid methanol and water entering coil 30a vaporizes at the elevated temperatures of combustion region 60 and enters the reforming region 62 as vapor.

Within reforming region 62 a reforming catalyst 102 (e.g., BASF catalyst K3-110 or ICI catalyst 52–8) reacts with the vaporized mix of methanol and water to produce hydrogen in the vicinity of the membrane tube 54. Membrane tube 54 is composed of one of a variety of hydrogen-permeable and hydrogen-selective materials including ceramics, carbon, and metals. Especially preferred materials for fabricating said membrane tube 54 are hydrogen-permeable palladium alloys, e.g., palladium alloyed with 35–45 wt % silver. Each end of membrane tube 54 is sealed by a metal cap 104. A metal gauze 106 within the reforming region 62 surrounds each cap 104 and maintains the catalyst 102 within region 62 and in the vicinity of membrane tube 54. A hydrogen stream 103 migrates by pressure differential through membrane tube 54 and into hydrogen transport region 64. A thin membrane tube 54 requires support against deformation under the pressure differential between reforming region 62 and hydrogen transport region 64. For this purpose, a tension spring 101 supports membrane tube 54 from within while allowing hydrogen stream 103 to pass by, into and along transport region 64.

Because a thin palladium alloy membrane may be used under the present invention, special construction methods have been developed under the present invention to make use of a delicate structure such as thin membrane tube 54. Under conventional practice, a thick palladium alloy membrane can be brazed because it can withstand the high temperatures and liquid phase aspects of brazing. A thin palladium alloy membrane, as proposed herein however, cannot be brazed under conventional methods because the elevated temperature and liquid brazing alloy destroy such thin palladium material. A thin membrane tube 54 could, under conventional practice for example, attach to end caps 104 and establish a gas-tight seal by use of gaskets and suitable support structures. As discussed more fully hereafter, under the present invention a thin palladium alloy membrane, e.g., tube 54, attaches to end caps 104 by first attaching a foil (not shown in FIG. 3), e.g., a copper or nickel foil, to the ends of tube 54 by ultrasonic welding and then brazing the foil-wrapped ends of tube 54 to end caps 104.

Hydrogen stream 103 travels within transport region 64 toward and into the open 56a of tube 56. Hydrogen stream 103 includes some impurities, e.g., carbon monoxide, carbon dioxide and unreacted methanol and water vapor, also traveling along transport region 64 and into innermost tube 56 at its open end 56a. All of hydrogen stream 103 enters the open end 56a of innermost tube 56.

Within tube 56 a polishing catalyst 110 reacts with impurities in the hydrogen stream 103 passing therethrough. Metal gauze 112 downstream from catalyst 110 holds catalyst 110 within tube 56. Polishing catalyst 110 (e.g., BASF catalyst G1-80 or ICI catalyst 23-1) reacts with certain impurities remaining in hydrogen stream 103, e.g., as much as 1% of carbon monoxide and carbon dioxide, and converts such impurities to innocuous byproducts, e.g., methane. Stream 103 of purified hydrogen and, now innocuous, byproducts passes through metal gauze 112 and exits reformer 12 at the outlet 14, i.e., at the opposite end 56b of tube 56.

Polishing catalyst 110 may be several separate catalysts within tube 56. In order to deal with carbon monoxide and carbon dioxide impurities, one uses a methanation catalyst. The process of methanation, i.e., reacting carbon monoxide or carbon dioxide with hydrogen to yield methane as shown below, is well known.

$$CO_2 + 4H_2 = CH_4 + 2H_2O$$

$$CO + 3H_2 = CH_4 + H_2O$$

Methanation provides an acceptable polishing step because methane is considered relatively inert or innocuous to the fuel cell 16 (FIG. 1) whereas carbon dioxide and carbon monoxide are poisonous to the fuel cell.

If reformer 12 uses methanol in the steam reforming step, and leaks in the membrane tube 54 allow carbon monoxide and carbon dioxide to pass into the hydrogen stream 103, some unreacted methanol and water vapor may exist in the hydrogen stream 103. To convert such unreacted methanol into a harmless byproduct prior to entering the fuel cell 16 (FIG. 1), a reforming catalyst which is a low temperature copper/zinc shift catalyst, is placed through a portion (e.g., one-fourth to one-third) of the polishing catalyst bed, i.e., innermost tube 56, followed downstream by a methanation catalyst.

The predominant chemical reaction for steam reforming methanol is shown below.

$$CH_3OH + H_2O = CO_2 + 3H_2$$

Returning to reforming region 62, steam reforming byproduct stream 105 moves toward closed end 52b of tube 52 and through critical orifice 120 serving as an outlet for tube 52 and discharging near air inlet 34. Optionally, deflector 57 directs the flow of byproduct stream 105 and air from inlet 34 toward combustion catalyst 100. Byproduct stream 105 thereby encounters and mixes with the air inflow 107 of air at inlet 34. Air inflow 107 may be preheated to enhance the catalytic ignition within combustion region 60. For example, an air heater 37 (FIG. 1) may be provided in series along the inlet 34 to reformer 12. Alternatively, inlet 34 may be routed through combustion region 60 as shown schematically in FIG. 3. The resulting mixture travels toward and through combustion catalyst 100 and ignites thereat. The combustion byproducts then travel through combustion region 60 and eventually, after heating coil 30a and thermally supporting the steam reforming process within region 62, exit reformer 12 at the combustion exhaust ports 38.

Reformer 12 operates at a relatively lower temperature than conventional steam reforming devices. Because reformer 12 continually purifies hydrogen as it is produced, the steam reforming reaction may be conducted well away from its equilibrium limitation. Although equilibrium limitations are generally not important in the case of steam reforming methanol, they are very important in the case of steam reforming methane (natural gas). Unreacted reactants in the relatively lower temperature reforming process tend to be eventually reacted due to the continuous siphoning of hydrogen from the process. Under the present invention, the steam reforming process may be operated at approximately 250 to 600 degrees Celsius. For methanol reforming the operating temperature of the reformer would be approximately 250 to 300 degrees Celsius.

To create an appropriate pressure differential at membrane tube 54, the liquid methanol and water should be pumped, i.e., provided by source 32, at approximately 6 to 20 atmospheres. The polishing step should be conducted at approximately one to three atmospheres within polishing region 66. The pressure within hydrogen transport region 64 is essentially equal to the pressure within polishing region 66. The reforming process should be operated at 6 to 20 atmospheres to provide a substantial pressure differential across membrane tube 54. Critical flow orifice 120 can be sized to provide a pressure drop from the reforming region 62 (6 to 20 atmospheres) to one atmosphere within the combustion region 60. The byproduct stream 105 thereby enters the combustion region 60 at approximately one atmosphere. This allows operation of the air supply at inlet 34 at approximately one atmosphere, and thereby allows use of an inexpensive air blower 36.

Dimensions for reformer 12 sufficient to feed a typical fuel cell 16 are relatively small. Ten liters per minute (21 cubic feet per hour) of hydrogen is sufficient to generate one kilowatt of electrical energy in fuel cell 16. A steam reformer 12 under the present invention sufficient to support a one kilowatt fuel cell 16 would be roughly three inches in diameter by 15 to 16 inches in length. To increase volumetric production, the length of reformer 12 could be increased or the diameter of reformer 12 could be increased. The volumetric production rate for reformer 12 is limited primarily by the area of membrane 56 exposed to the reforming process. Increasing the length of reformer 12 or the diameter of reformer 12 increases the exposed area of membrane tube 54 and thereby increases hydrogen output for reformer 12. However, multiple standard-sized reformers 12 may be employed in parallel within a common combustion zone.

FIG. 4 illustrates schematically the architecture of an alternate reformer 12' with an enlarged outermost metal tube 50' defining a common combustion region 60'. Within the relatively larger combustion region 60', a plurality of reformer tubes 51, i.e., each a combination of a tube 52, a tube 54, and a tube 56, are arranged in spaced relation. While not shown in FIG. 4 for purposes of clarity, reformer 12' would include a feedstock inlet, a product hydrogen outlet, and a combustion gas outlet. A common air inlet 34 supplies air to the common combustion A region 60'. As may be appreciated, each of reformer tubes 51 provides a byproduct stream 105 (not shown in FIG. 4) to the common combustion region 60'.

Returning to FIG. 3, reformer 12 must be initiated to operate. Generally, the reforming region 62 must be elevated to approximately 150 to 200 degrees Celsius if methanol is the feedstock, or 300 to 500 degrees Celsius if hydrocarbons are the feedstock. Once the reforming process begins, the byproduct stream 105, including by design a given amount of hydrogen as combustion fuel, enters the combustion region 60, encounters combustion catalyst 100, and combusts to thermally support the steam reforming process. The combustion catalyst only needs hydrogen present (mixed with air) to ignite the byproduct stream 105. The goal in starting reformer 12, therefore, is to elevate the reforming region 62 to approximately 150 to 200 degrees Celsius (in the case of methanol reforming).

A simple cartridge-type electric resistance heater 140, either inserted into the reforming catalyst 102 or, as illustrated in FIG. 3, into the center of tube 56 initiates operation of reformer 12. Alternatively, a resistance heater may be used to heat the methanol and water feed provided at inlet 30. In either event, once the reforming catalyst 102 reaches a sufficiently high temperature (150 to 200 degrees Celsius) the reforming reaction begins and the combustion catalyst 100 reacts with hydrogen present in byproduct stream 105. At this point, the electrical resistance heater 140 can be shut down. A 50 to 100 watt resistance heater 140 should be adequate, based on conventional thermal mass calculations, to sufficiently heat the reforming region 62 in a matter of minutes.

FIG. 5 illustrates, partially and in cross section, an alternate form of the present invention with its combustion system distributed through the reformation region to improve heat transfer from the combustion process to the reformation process. In FIG. 5, reformer 212 is a steam reformer with internal hydrogen purification receiving at its inlet 230 a feed stock, e.g., methanol and water, and providing at its outlet 214 purified hydrogen for application to, for example, a fuel cell (not shown in FIG. 5). As with earlier embodiments of the present invention, reformer 212 leaves a selected portion of hydrogen in its byproduct stream to support the combustion process. Combustion byproducts exit at the exhaust port 238.

Reformer 212 includes an outer metal tube 252 sealed at each end by end plates 253, individually 253a and 253b and gaskets 255, individually 255a and 255b. Bolts 257 secure end plates 253 against the shoulders 252, individually, 252a and 252b, at each end of tube 252. A hydrogen purification module lies within and generally concentric to tube 252 and includes a thin palladium alloy membrane tube 254 sealed by end caps 304a and 304b. Alternatively, membrane tube 254 may be comprised of hydrogen-selective and hydrogen-permeable materials other than palladium alloys, including porous carbon, porous ceramics, hydrogen-permeable metals other than palladium, porous metals, and metal-coated porous carbon and porous ceramics and porous metals. As may be appreciated, tube 254 and caps 304 may be supported in some fashion (not shown) within tube 252. End cap 304*b* communicates with outlet 214 through plate 253*b* and the product hydrogen stream 303 emerges from outlet port 214. A polishing catalyst bed, preferably a methanation catalyst, is located at the permeate side of membrane tube 254 (not shown) as discussed earlier and shown in FIG. 3.

Inlet 230 passes through wall 253*a* and couples to a vaporization coil 230*a*. Outlet 231 of coil 230*a* feeds directly into the reformation region 262 defined as being within tube 252 but external of tube 254. Also located within and distributed throughout the reformation region 262 is a combustion coil 250. In the particular embodiment illustrated, coil 250 surrounds in spiral fashion membrane tube 254 and extends substantially throughout the entire reformation region 262. A combustion catalyst 302 lies within and either along the length of coil 250 or localized within coil 250 at or near end 250*a*. End 250*a* of 250 receives a fuel stock, as described more fully hereafter, and combustion occurs within 250 as the fuel stock travels along 250 and encounters the combustion catalyst 302 therein. Because 250 extends uniformly throughout the reformation region 262 and because 250 provides significant surface area, rapid and well distributed heat transfer occurs from the combustion process occurring within 250 to the surrounding reformation region 262.

Reformation region 262 couples through wall 253*b* at its outlet 220 to a conduit 221. Conduit 221 carries the byproduct stream 205, i.e., the byproduct of hydrogen reformation including a selected amount of hydrogen intentionally not taken across the membrane tube 254, to the combustion process. Conduit 221 delivers byproduct stream 205 to a pressure let down valve 223. Byproduct stream 205 then continues, at lowered pressure, into an intake manifold 207. Manifold 207 includes an air inlet 209, e.g., coupled to an air blower or to discharged air from the cathode component of the fuel cell (not shown in FIG. 5), and air passage way 211 carrying combustion air to a mixing region 213 at or near the inlet 250*a* of combustion coil 250. The combustion fuel stock as provided by the byproduct stream 205, thereby mixes with the incoming combustion air in mixing region 213 and enters end 250*a* of combustion coil 250. Combustion catalyst 302 within 250 ignites the fuel stream 205 and heat transfers efficiently and rapidly in well distributed fashion into and throughout the reformation region 262.

Figure 7:
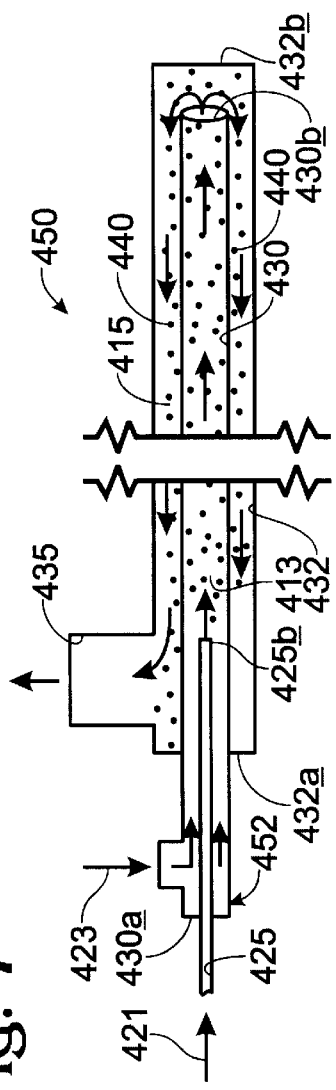
FIG. 7 illustrates schematically a combustion system applicable to the present invention and providing along its length a generally uniform temperature gradient.

While a coil or spiral form of combustion system has been illustrated, i.e., the coil 250, other shapes may be employed as a combustion system within the reformation region 262. For example, generally tubular structures may assume a variety of forms for distribution throughout reformation region 262. As discussed more fully hereafter, a countercurrent combustion system as illustrated in FIG. 7 establishes improved, i.e., uniform, heat distribution throughout reformation region 262. Thus, the advantage of distributing a combustion system throughout the reformation region 262 may be achieved in a variety of specific configurations.

In steam reformer 12 (FIG. 3), the combustion process occurred in a region surrounding the reformation region, i.e., externally of the tube 52 (FIG. 3) thereby requiring heat transfer into and across metal tube 52. From the inner surface of tube 52, heat transfer then occurred by migration across the reformation region. In steam reformer 212, however, heat generated within and distributed throughout the reformation region 262, i.e., within the coil 250, better transfers more rapidly throughout the reformation region 262. In essence, the combustion process has been brought into and distributed throughout the reformation region 262. Heat transfer improves because the flow of reformation gasses passes directly over and around coil 250. Generally, coil 250 provides significantly greater surface area for heat transfer between combustion and reformation as compared to the surface area provided by tube 52 in reformer 12. Heat energy need not transfer into and migrate across the reformation region, but rather generates within the reformation region and radiates outward throughout the reformation region.

Figure 6:
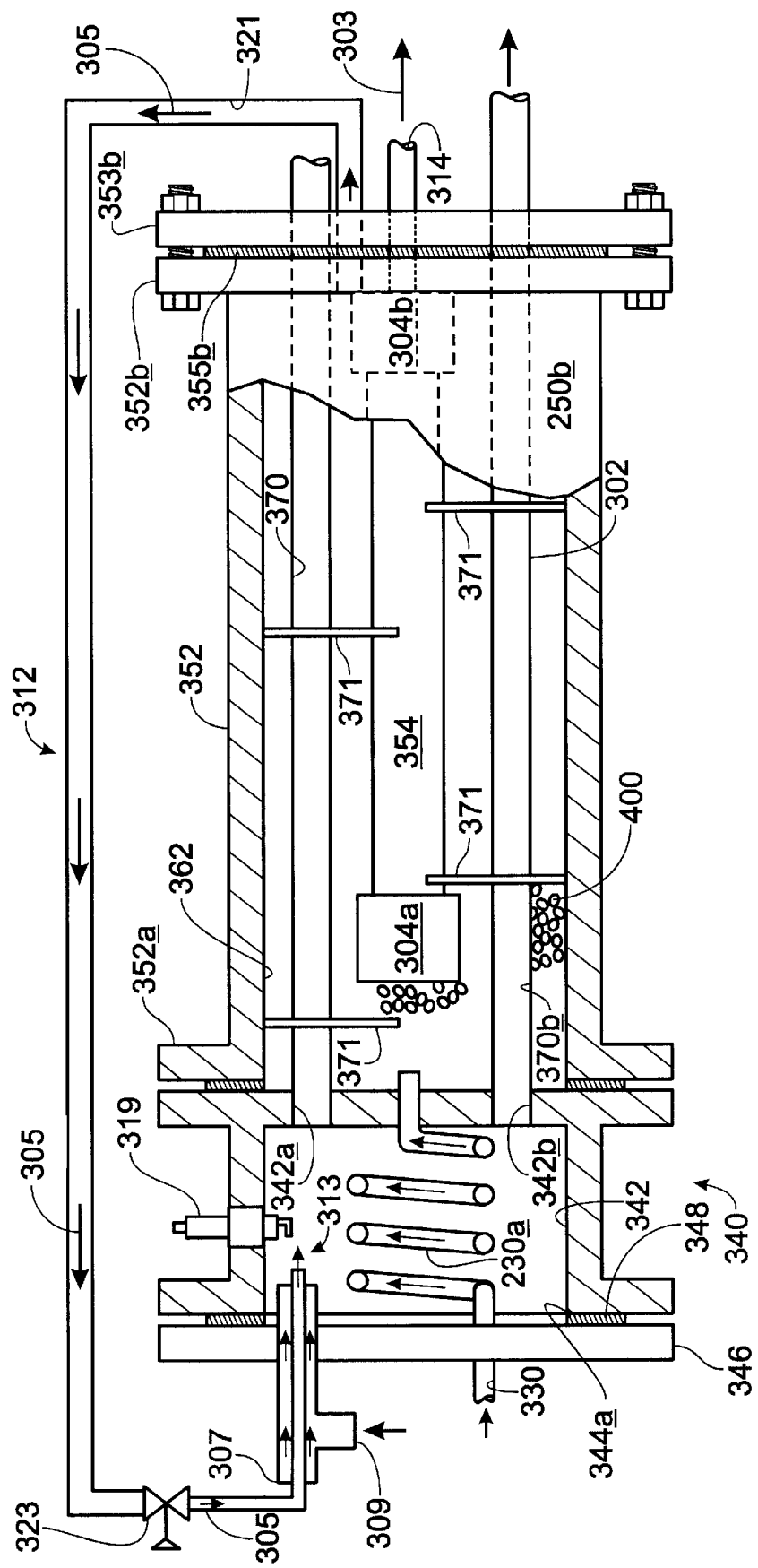
FIG. 6 illustrates schematically and partially in cross section another embodiment of a steam reformer with internal hydrogen purification according to the present invention including an isolated vaporization chamber.

FIG. 6 illustrates another embodiment of the present invention, also distributing combustion heat energy throughout the reformation region, but further providing the advantage of isolating the vaporization process from the reformation process. Generally, a preferred temperature for vaporization of the feed stock, e.g., 400–650 degrees Centigrade, is greater than a preferred temperature, e.g., 250–500 degrees Centigrade, for hydrogen reformation. In FIG. 6, steam reformer 312 includes an outer metal tube 352 defining therein a reformation region 362. Tube 352 includes shoulders 352 at each end, individually 352*a* and 352*b*. A vaporization module 340 attaches to shoulders 352*a* of tube 352. Module 340 defines a vaporization chamber 342 isolated relative to reformation region 362. More particularly, module 340 includes a generally cylindrical barrel 344 having an open end 344*a* and a closed end 344*b*. An end plate 346 and gasket 348 seal vaporization chamber 342, i.e., close the otherwise open end 344*a* of barrel 344. The closed end 344*b* of barrel 344 couples to shoulders 352*a* of tube 352. In this manner, closed end 344*b* together with a gasket 350 seal the end of tube 352 and, thereby, seal reformation chamber 362. By isolating vaporization chamber 342 and reformation chamber 362, vaporization occurs at preferred, i.e., significantly higher, temperatures than temperatures preferred for reformation chamber 362.

Inlet 330 passes through end plate 346 and feeds into coil 230*a* as located within vaporization chamber 342. The distal end of coil 230*a* then passes through closed end 344*b* of barrel 344 and feeds into reformation chamber 362. In this manner, vaporized feed stock, i.e., methanol and water vapor, enter region 362 and chemically interact with reformation catalyst 400 distributed throughout reformation region 362.

Vaporization chamber 342 includes outlets passing combustion exhaust along corresponding conduits 370 extending through combustion region 362. In this manner, the heat energy of the combustion exhaust transfers through conduits 370 and into the reformation region 362. Again, distributing heat energy throughout and within the reformation region improves heat transfer distribution and rate. For example, vaporization chamber 342 includes outlets 342*a* and 342*b* passing combustion gas into corresponding conduits 370*a* and 370*b*. The combustion exhaust remains isolated relative to the combustion region 362, but the heat energy of the combustion exhaust migrates through conduits 370 and into the combustion region 362. Conduits 370 pass through an end plate 353*b*, secured to shoulders 352*b*, and the combustion exhaust releases to atmosphere. Heat transfer can be improved, and the degree of resistance to flow and turbulence along the exterior conduits 370 can be controlled by use of baffles 371.

As in previously described embodiments, reformation occurring in reformation region 362 supports migration of hydrogen across a tubular palladium alloy membrane 354. Other hydrogen-permeable and hydrogen-selective compositions that may be used in place of palladium alloys for membrane 354 include porous carbon, porous ceramic, hydrogen-permeable metals, porous metals, and metal-coated porous ceramics and porous carbon and porous metal. Tubular membrane 354, sealed at each end by means of end caps 304, feeds the product hydrogen stream 303 at the outlet 314 of reformer 312. A polishing catalyst bed (not shown) is located at the permeate side of membrane 354 as shown in FIG. 3. A preferred polishing catalyst is a methanation catalyst.

By intentionally not recovering all hydrogen available in the reformation region 362, the remaining hydrogen sweeps away in the byproduct stream 305 and provides a fuel stock for the vaporization module 340. More particularly, reformation region 362 couples to a conduit 321 passing through end plate 353*b*. Conduit 321 carries the byproduct stream 305, including a selected amount of hydrogen remaining therein as fuel stock. Conduit 321 passes through a pressure let down valve 323 and provides the reduced-pressure fuel stock flow 305' to an inlet manifold 307. Inlet manifold 307 operates in similar fashion to the inlet manifold 207 of FIG. 5, i.e., receiving combustion air and promoting mixing of the combustion air and reduced-pressure byproduct stream 305'. As the combined combustion air and stream 305' intermix at the mixing region 313, an igniter 319 triggers combustion thereof. Igniter 319 may be a variety of devices, e.g., glow plug, spark plug, catalyst, and the like. In the preferred form of the reformer 312, however, a high voltage spark ignition or possibly a glow plug is considered preferred as igniter 319 for long term reliability and ease of replacement.

In addition to isolation of vaporization, reformer 312 also provides the advantage of a preferred low pressure drop between the initiation of combustion and exhaust from the combustion region. The architecture of reformer 312 provides a lower pressure combustion process because conduits 370 are generally straight conduits offering reduced and controlled resistance to the flow of combustion exhaust gasses. With a lower pressure combustion process, combustion air, e.g., such as is provided at inlet 309 of intake manifold 307, may be provided by a relatively lower pressure and relatively less expensive air blower (not shown in FIG. 6).

FIG. 7 illustrates schematically an alternate combustion system applicable to the various embodiments of the present invention. In FIG. 7, a double-walled counter current combustor 450 includes an inlet manifold 452 receiving a byproduct stream 421 and an air stream 423. Byproduct stream 421 is taken from a reformation process as a byproduct, but includes a selected amount of hydrogen intentionally left therein as a fuel stock for combustion. Byproduct stream 421 travels along an inner conduit 425 and exits conduit 425 in a mixing region 413. Air stream 423 travels along manifold 452, generally surrounding and parallel to inner conduit 425 and encounters byproduct stream 421 in mixing region 413. Mixing region 413 comprises an inner tube 430 carrying therealong the mixture of combustion air, i.e., air stream 423 and fuel gas, i.e., byproduct stream 421. Tube 430 is closed at one end, i.e., end 430*a* forming a portion of manifold 452. The open end 430*b* of tube 430, however, releases mixed fuel gas and combustion air into an outer mixing region 415. Outer mixing region 415 is defined by an outer tube 432. Tube 432 is closed at each of its ends 432*a* and 432*b* with manifold 452 passing through end 432*a*. A combustion catalyst 440 is distributed throughout regions 413 and 415. Alternately, combustion catalyst 440 may be localized within tube 430 at or near mixing region 413.

The highest temperature combustion occurs when the mixture of fuel gas and combustion air first encounter catalyst 440, i.e., at the outlet of manifold 452. As the gas mixture continues along tube 430 and encounters catalyst 440 therealong, continued combustion occurs but generally at progressively lower temperatures. As the gas mixture continues out of tube 430, at its open end 430*b*, it reverses direction and travels back along tube 432 and encounters more catalyst 400. As a result, heat energy is produced along the length of tubes 430 and 432 and exhaust gasses exit at the exhaust port 435.

Generally, a significant temperature gradient exists along a combustion catalyst bed, the hottest portion being where the fuel gas and combustion air first encounter the combustion catalyst or igniter device. Such significant temperature gradient can be undesirable, especially when applying the heat energy to a reformation process most desirably conducted at uniform temperature throughout. Under the present invention, combustor 450 provides a more uniform temperature gradient along its length as compared to a conventional combustion bed. The hottest gasses within combustor 450, i.e., near manifold 452, release heat energy through tube 430 and into the coolest gasses within combustor 450, i.e., near exhaust port 435. By thermally coupling the hottest portion of the gasses with the coolest portion of the gasses a more uniform overall temperature gradient exists along combustor 450.

Figure 8:
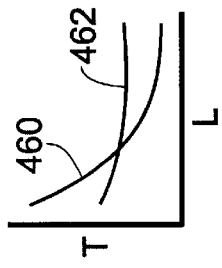
FIG. 8 illustrates the temperature gradient of the combustion system of FIG. 7 as compared to a conventional temperature gradient.

FIG. 8 illustrates a relationship between the length L of a combustion bed (x axis) and temperature T therealong (y axis). Curve 460 in FIG. 8 illustrates substantially higher temperatures at the beginning of a conventional combustion bed and a significant drop in temperature throughout the conventional combustion bed. Curve 462, however, illustrates the more uniform, i.e., more flat, temperature gradient obtained by use of combustor device 450. More particularly, a shallow and fairly level curve 462 indicates a uniform temperature along the length of combustor 450. Accordingly, combustor 450 provides a more uniform dispersal of heat energy into a reformation region.

While illustrated as a generally straight device in FIG. 7, it will be understood that the double-walled architecture of the combustion device 450 may be formed in alternate shapes, e.g., spiral, and applied to the various embodiments of the present invention as a combustion system.

In addition to alternate combustion and vaporization features, alternative methods of hydrogen purification may be employed in a steam reformer under the present invention. In addition to tubular and concentric-tubular architectures, planar membrane structures may also be employed in a steam reformer with internal hydrogen purification.

Figure 9:
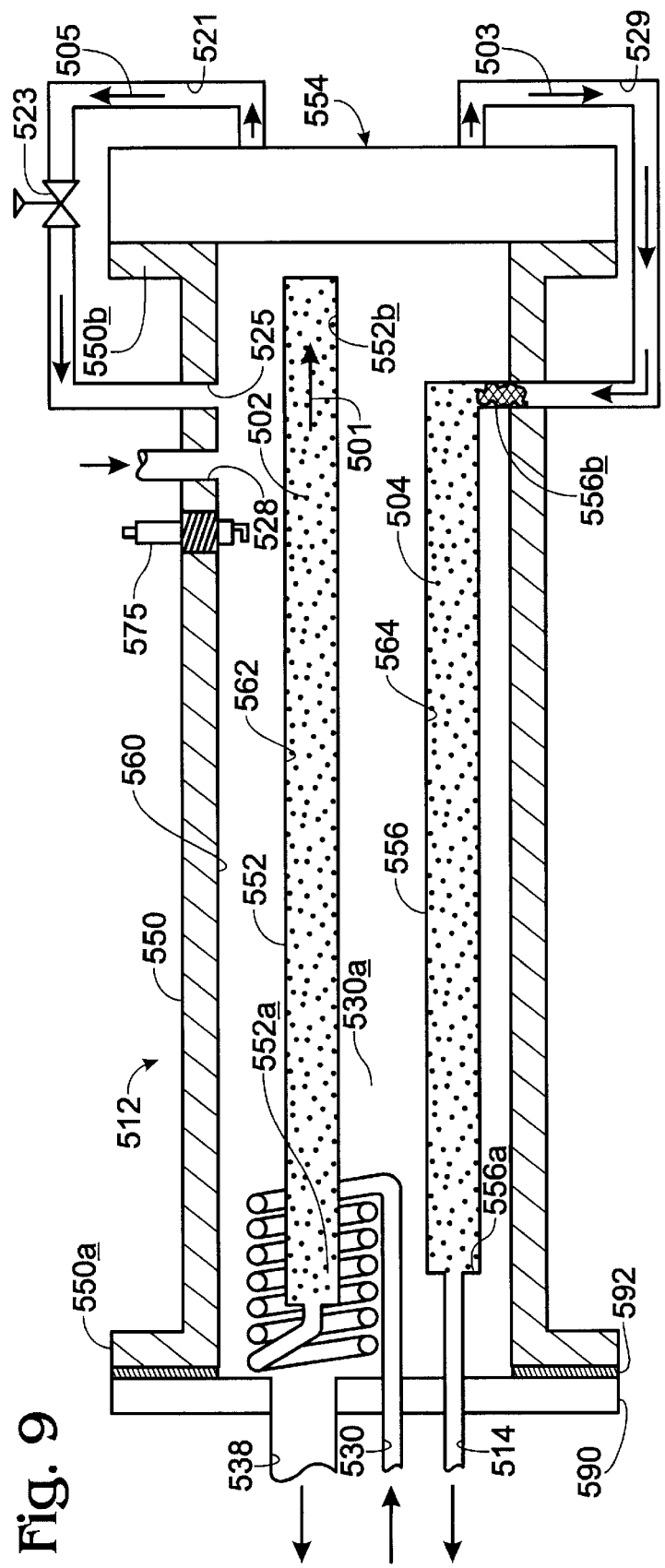
FIG. 9 illustrates another form of steam reformer with internal hydrogen purification under the present invention using plate membrane elements.

FIG. 9 illustrates schematically a further embodiment of a steam reformer with internal hydrogen purification according to the present invention and using planar membrane structures. In FIG. 9, reformer 512 includes an outer metal tube 550 having shoulders 550*a* and 550*b* at each open end thereof. Within tube 550, a metal reforming catalyst tube 552 and a metal polishing catalyst tube 556 lie in generally parallel relation along the length of tube 550. As may be appreciated, however, a variety of geometric configurations and relationships between tubes 552 and 556 may be employed. Reforming catalyst tube 552 contains a reforming catalyst 502 and establishes a reformation region 562. Similarly, polishing catalyst tube 556 contains a polishing catalyst 504 and establishes a polishing region 564. An end plate 590 and gasket 592 couple to shoulder 550*a* and seal tube 550. Inlet port 530 carries a liquid feed stock, e.g., methanol and water, through end plate 590 and into vaporization coil 530a. In the particular embodiment illustrated, coil 530 wraps about one end of tube 552 and sits near the combustion exhaust port 538 provided in end plate 590. Vaporization coil 530a couples to end 552a of tube 552 whereby vaporized feed stock exits coil 530a and enters reformation region 562.

A plate membrane module 554 couples to shoulder 550b and seals end 550b of tube 550 to complete a combustion region 560 within tube 550, but external of tubes 552 and 556. Plate membrane module 554 couples to tube 552 to receive a reformate-rich gas flow 501, couples to conduit 529 to provide a product or hydrogen stream 503, and couples to conduit 521 to provide a byproduct stream 505 as fuel stock to support combustion in region 560. More than one tube 552 may be used. Byproduct stream 505, as in earlier-described embodiments of the present invention, intentionally includes a given amount of hydrogen not taken from the reformation process and applied to the combustion process. Conduit 521 carries byproduct stream 505 from plate membrane module 554 through a pressure let down valve 523 and into combustion region 560 at the inlet port 525 thereof. Adjacent fuel inlet port 525, an air inlet port 528 admits air, e.g., forced by blower (not shown), into combustion region 560. Alternatively, a manifold, as in earlier-described embodiments of the present invention, may be used to admit air and byproduct stream 505 into combustion region 560. As the byproduct stream 505 enters region 560, and intermixes with the combustion air at port 528, it continues past an igniter 575. Igniter 575 initiates combustion of the mixture of byproduct stream 505 and combustion air thereby supporting a combustion process within combustion region 560. As may be appreciated, heat developed in this combustion process supports vaporization of feed stock in the vaporization coil 530a and thereby provides vaporized gasses to the reformation region 562. Heat from combustion in region 560 also serves to directly heat the reforming region 562 and to heat the polishing region 564.

Conduit 529 carries the product (hydrogen) stream 503 into end 556b of polishing catalyst tube 556. More than one conduit 529 and more than one tube 556 may be used. Product stream 503 passes through the polishing region 564, where undesirable elements are neutralized, and the final purified hydrogen product passes from the end 556a of tube 556 and out the outlet port 514. For example, when the polishing catalyst 504 is a methanation catalyst, carbon monoxide and carbon dioxide present in product stream 503 are converted to methane as described previously.

Figure 10:
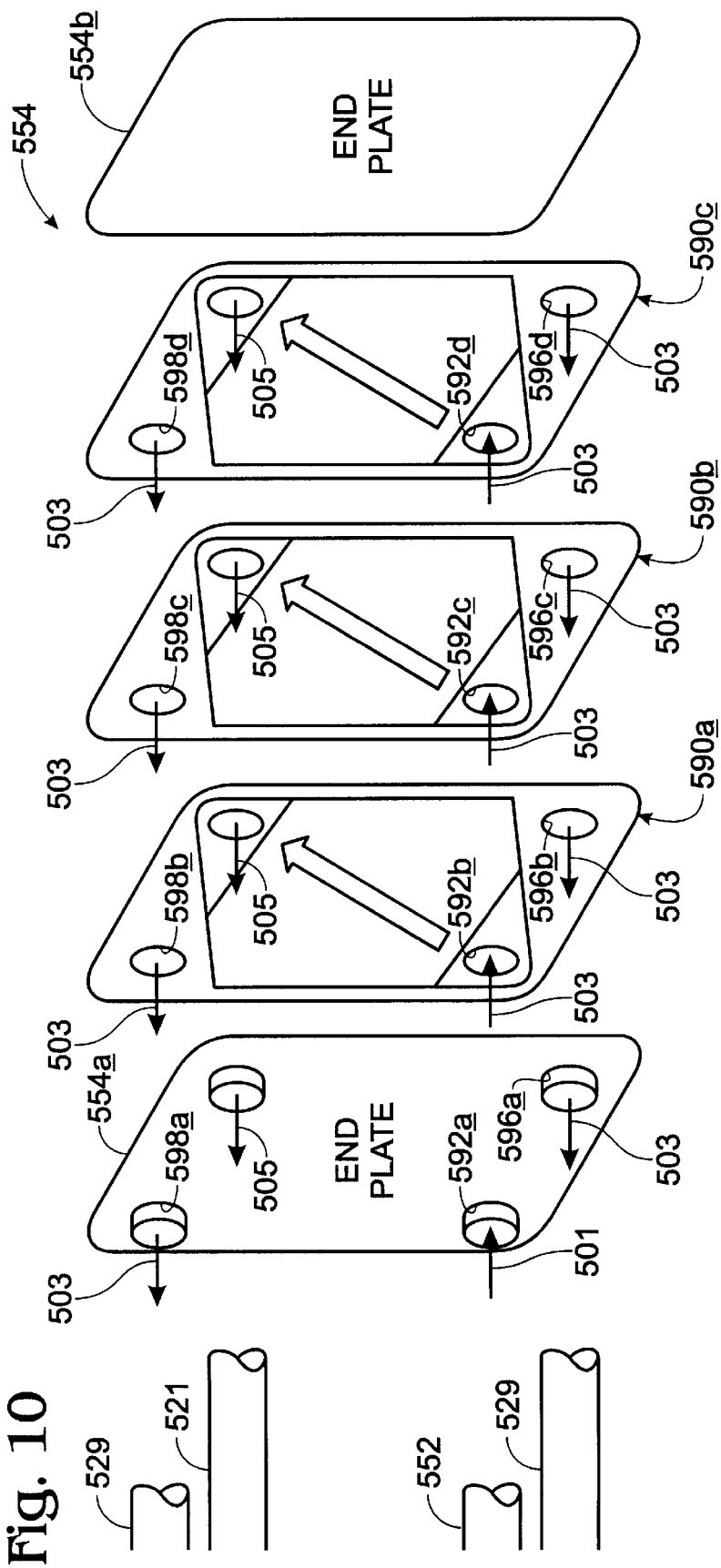
FIG. 10 illustrates in exploded view a plate membrane module of the steam reformer of FIG. 9 including membrane envelope plates.

FIG. 10 illustrates in exploded view the plate membrane module 554 and its relationship to tube 552 and to conduits 521 and 529. Plate membrane module 554 includes end plates 554a and 554b. A series of membrane envelope plates 590 stack between end plates 554. In the particular embodiment of the invention illustrated in FIG. 10, three such membrane envelope plates 590, individually 590a–590c, stack between end plates 554. End plates 554a and 554b and membrane envelope plates 590 are all generally rectangular and have corresponding dimensions. Other geometries, such as circular, may be used rather than the rectangular geometry shown. In other words, plates 554a–554b and 590a–590c stack like a deck of cards and couple together, e.g. by brazing, to form module 554. End plate 554b is a solid planar structure. End plate 554a, however, includes inlet and outlet ports for coupling to other portions of reformer 512. In particular, reformation catalyst tube 552 couples to a reformate-rich inlet port 592a to receive the products of reformation, i.e., to receive the reformate rich flow 501. Conduit 521 couples to a reformate-depleted outlet port 594a to take from module 554 the byproduct stream 505. In the particular embodiment illustrated, module 554 has two product outlet ports, individually 596a and 598a, providing product stream 503. However, only one product outlet port may be used in some embodiments. Conduit 529, shown twice in FIG. 10, couples to ports 596a and 598a to collect the product stream 503 therefrom. All of the ports 592a, 594a, 596a, and 598a, need not be located on end plate 554a. Rather, one or more of the ports may be located on end plate 554b as desired or necessary in a particular configuration.

Each membrane envelope plate 590 includes ports positioned in locations corresponding to ports 592a, 594a, 596a, and 598a of end plate 554a. When stacked and operating as the plate membrane module 554, these various ports align and provide conduits to and from the filtration process executed by module 554. Each of plates 590a–590c include a product port 598, individually 598b–598d. Ports 598a–598d align and cooperate to provide a conduit for product stream 503 out of module 554 and into conduit 529. As will be explained more fully hereafter, the product, i.e., hydrogen, enters ports 598b–598d laterally within the corresponding membrane envelope plate 590. Each of membrane envelope plates 590a–590c include also a port 596, individually 596b–596d, aligned with outlet port 596a of end plate 554a. Ports 596a–596d also carry product stream 503 away from plate membrane envelopes 590 and into conduit 529. As with ports 598b–598d, ports 596b–596d receive the hydrogen stream 503 laterally from within the corresponding membrane envelope plate 590.

Ports 592b–592d align with port 592a of end plate 554 and thereby provide a conduit for introduction of the hydrogen-rich reformate flow 501 from tube 552 and into membrane envelope plates 590. Each of plates 590a–590c include a byproduct port 594b–594d. Ports 594b–594d align with port 594a of end plate 554a to provide a conduit for the byproduct stream 505 away from membrane envelope plates 590. Forcing the hydrogen-rich reformate flow 501 into port 592a produces the byproduct flow 505 at port 594a for application to the combustion process within combustion region 560 and produces the product stream 503 for application to the polishing region 564.

Figure 11:
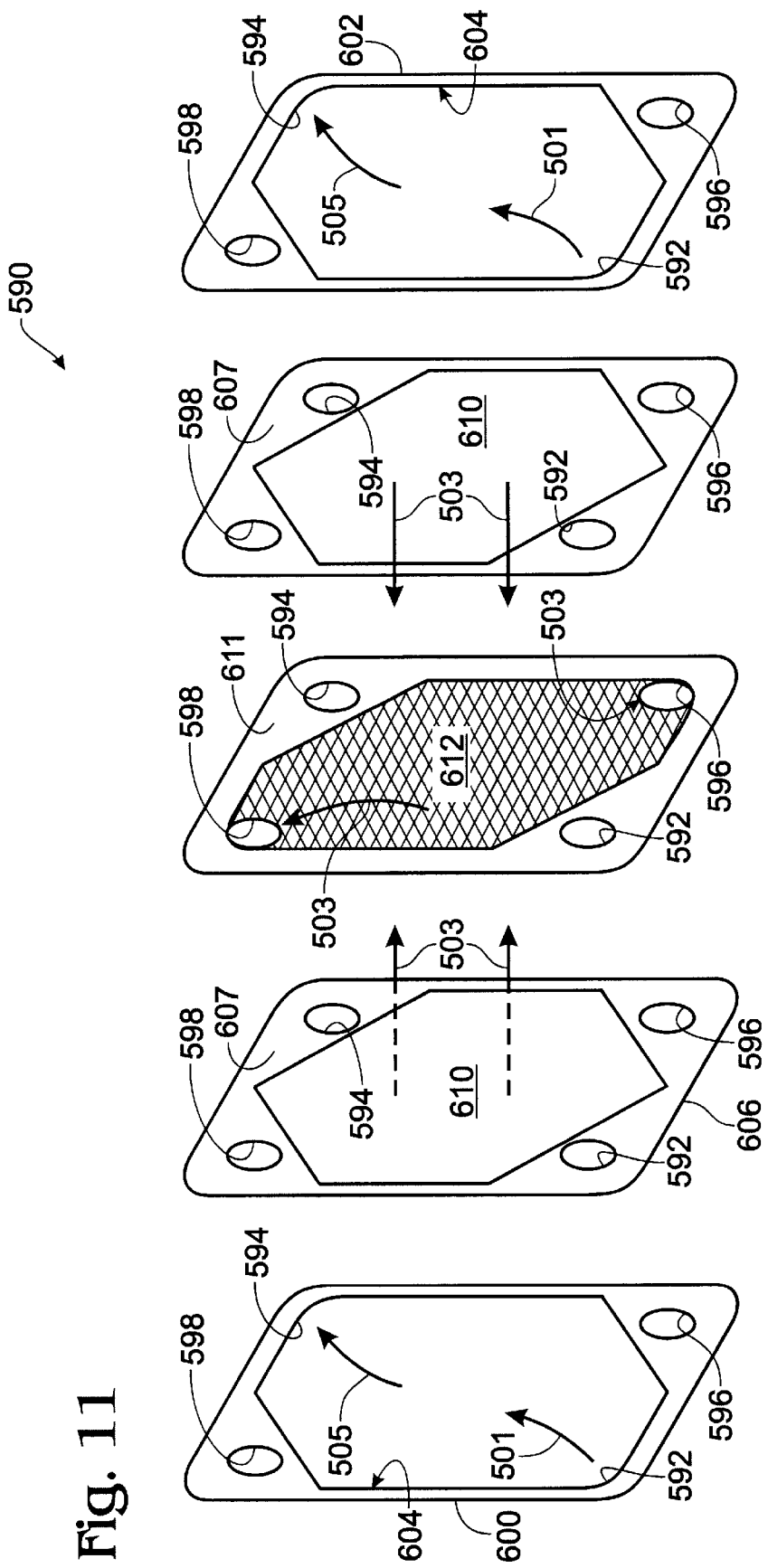
FIG. 11 illustrates in exploded view a membrane envelope plate of FIG. 10.

Each of the membrane envelope plates 590 itself includes a stack of individual plate elements. FIG. 11 illustrates in exploded view the set of plate elements found in each of the membrane envelope plates 590. In FIG. 1, each of the plate elements include ports establishing communication through the membrane envelope 590 as described above in connection with FIG. 10. Some of these ports, however, are "open" laterally into the corresponding plate element and thereby provide lateral access to portions of module 554.

Each membrane envelope plate 590 includes a left spacer plate 600 and right spacer plate 602 as the outer most plates in the stack. Generally, each of spacer plates 600 and 602 are "frame" structures defining an inner open region 604. Each inner open region 604 couples laterally to ports 592 and 594. Port 592 thereby admits flow 501 into open region 604 and port 594 thereby carries byproduct stream 505 out of open region 604. Ports 596 and 598, however, are closed relative to open region 604 thereby isolating the product stream 503.

Each membrane envelope plate 590 also includes a left membrane plate 606 and a right membrane plate 608, each adjacent and interior to a corresponding one of plates 600 and 602. Membrane plates 606 and 608 each include as a central portion thereof a palladium alloy membrane 610 secured to an outer metal frame 607. In plates 606 and 608, all of the ports 592, 594, 596, and 598 are closed relative to the palladium alloy membrane 610. Each palladium alloy membrane 610 lies adjacent to a corresponding one of open regions 604, i.e., adjacent to the hydrogen-rich reformate flow 501 arriving by way of port 592. This provides opportunity for hydrogen to pass through the palladium alloy membrane 610 of the adjacent membrane plate 606. The remaining gasses, i.e., the byproduct stream 505, leave open region 604 through port 594.

A screen plate 609 lies intermediate membrane plates 606 and 608, i.e., on the interior or permeate side of each of membranes 610. Screen plate 609 includes an outer frame 611 and carries in a central region thereof a screen 612. Ports 592 and 594 are closed relative to the central region of screen plate 609, thereby isolating the byproduct stream 505 and the reformate-rich flow 501 from the product stream 503. Ports 596 and 598 are open to the interior region of plate screen 609 carrying screen 612. Hydrogen, having passed through the adjoining membranes 610, travels along and through screen 612 to the ports 596 and 598 and eventually to conduit 529 as the product stream 503.

As the hydrogen-rich reformate flow 501 enters port 592a and forces its flow against membranes 610, hydrogen passes therethrough as the product stream 503 and along ports 596 and 598. The byproduct stream 505 diverts at the membranes 610 and travels along port 594 to conduit 521.

A variety of methods, including brazing, gasketing, and welding, may be used, individually or in combination, to achieve gas-tight seals between plates 600, 602, 606, 608, and 609, as well as between membrane envelopes 590a–c.

Screen 612 not only provides a flow path for the product flow 503, but also bears the pressure differential applied to membranes 610 to force hydrogen, i.e., product stream 503, across membranes 610. While illustrated only as a screen structure in FIG. 11, it will be understood that a variety of structures may be used within an open region of screen plate 609 to provide the support function against pressure applied to membranes 610 and to provide a flow path for product stream 503. To the extent that palladium alloy membranes 610 are better supported by an appropriate structure, e.g., screen 612, thinner and less expensive palladium alloy membranes 610 may be employed. Alternative materials to screen 612 include porous ceramics, porous carbon, porous metal, ceramic foam carbon foam, and metal foam.

As discussed throughout this specification, use of thin, less expensive palladium alloy membranes significantly reduces the cost of a steam reformer under the present invention. While it is recognized that use of such thin palladium alloy membranes will result in some contaminants passing into the product stream 503, subsequent purification steps may be taken, e.g., such as illustrated in several embodiments of the present invention.

Manufacturing steps taken in manipulation of the thin palladium alloy membranes, particularly in establishing a gas-tight seal relative to such membranes, must take into account the delicate nature of such thin palladium alloy membranes. In particular, conventional welding or brazing manufacturing steps, i.e., steps including a liquid-phase, cannot by applied to extremely thin (typically <50 microns) palladium alloy membranes. In particular, when liquid phase material contacts the thin palladium alloy membrane it dissolves and melts the membrane and, due to the extremely thin nature of the membrane, cannot serve as an acceptable manufacturing step. There are a variety of ways to establish a gas-tight seal relative to a thin palladium alloy membrane, however, the subject matter of the present invention proposes a particular method of manufacturing to achieve a gas tight seal of a thin palladium alloy membrane without causing significant damage to, i.e., leaks in, the palladium alloy membrane.

Under the present invention, a palladium alloy membrane may be attached and form a gas tight seal relative to an adjoining structure by means of an intermediate foil attached by ultrasonic welding. The method of manufacture proposed herein may be applied to the tubular form of membrane modules, e.g., such as shown in FIG. 3, or to plate form membrane structures such as shown in FIG. 11. Membrane tube 54 may then be coupled by brazing the foil to end caps 304. In the plate membrane form of the present invention, membranes 610 carrying a foil may be attached by brazing the foil to the surrounding frame 607 of plates 606 and 608. When applied to joining metals, ultrasonic welding strips away and cleans the metal surfaces to such extent that contact between such ultra-clean metals results in joining by solid state intermetallic diffusion. The ultrasonic action scrubbing the mating surfaces of the materials may be done under pressure such as 20 to 60 psi. Once these materials contact, the metal atoms diffluse together and thereby establish a gas tight seal. Important to note, ultrasonic welding does not require a liquid phase and when properly executed does not present opportunity for deterioration of a thin palladium alloy membrane. Because of the relatively low temperature requirements of ultrasonic welding, very little warping of material occurs. Accordingly, ultrasonic welding is particularly well suited for establishing a gas tight seal relative to an ultra thin palladium alloy membrane.

Under the disclosed embodiment of the present invention, ultrasonic welding is used to attach a copper or nickel alloy foil to the surface of the thin palladium alloy membrane. Once this additional copper or nickel alloy layer has been attached it is brazed or welded to an adjoining material, e.g., end caps 304 or frames 607.

Figure 12:
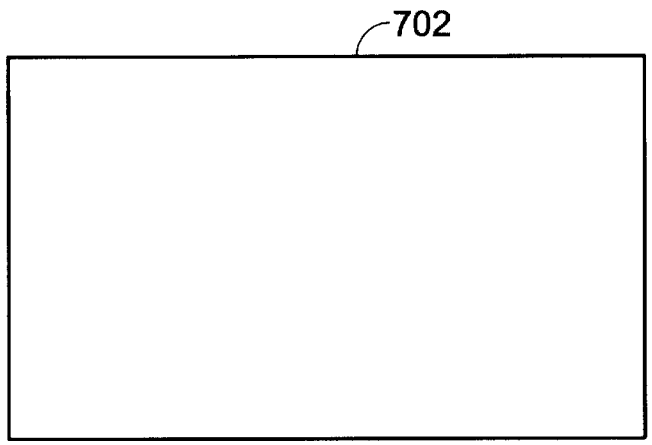
FIGS. 12–17 show membrane components for a tubular metal membrane module and assembly steps in the production of a tubular membrane module using manufacturing steps according to the present invention.
Figure 13:
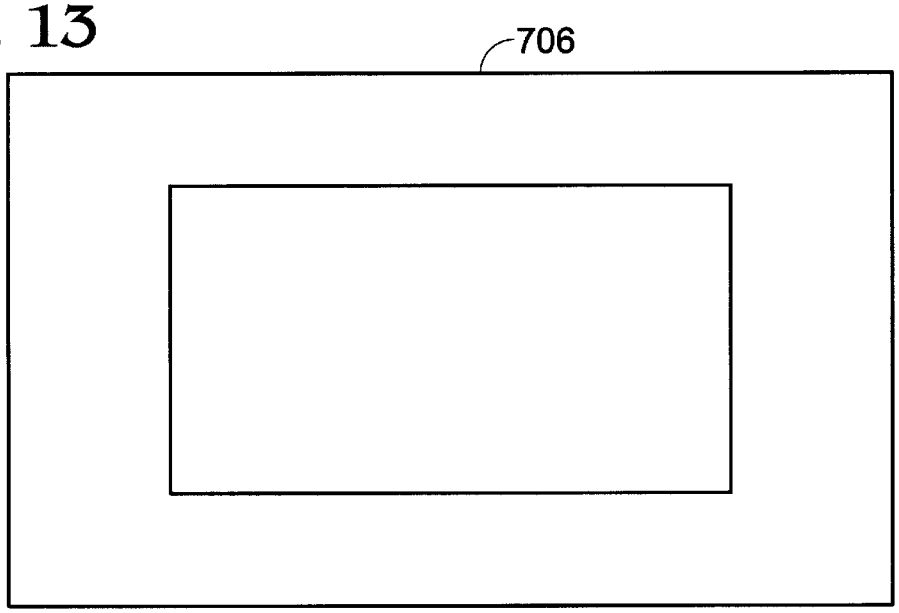
Figure 14:
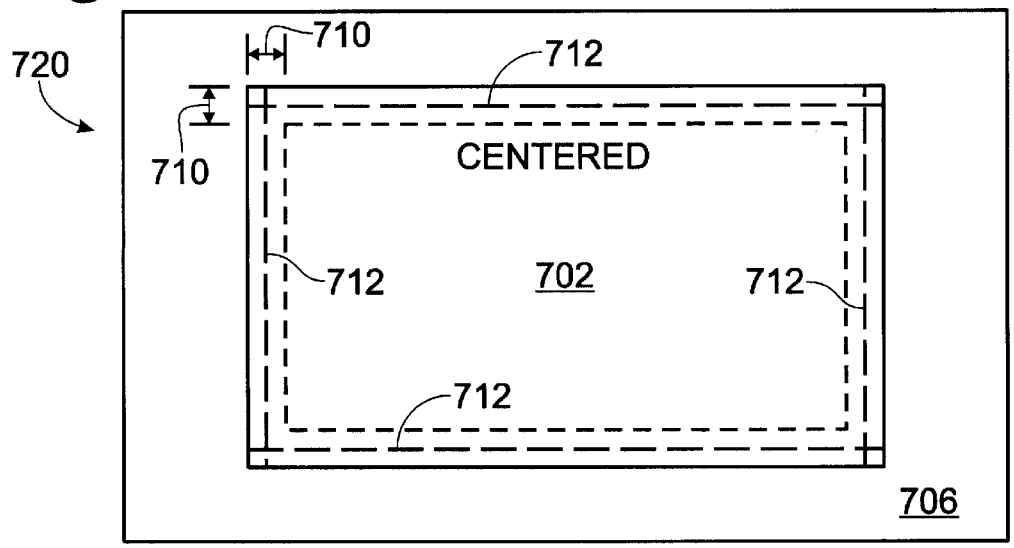
Figure 15:
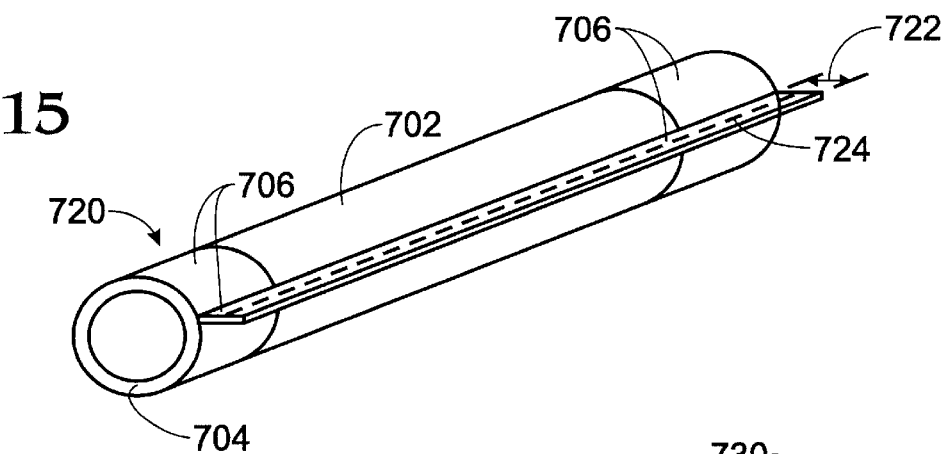
Figure 16:
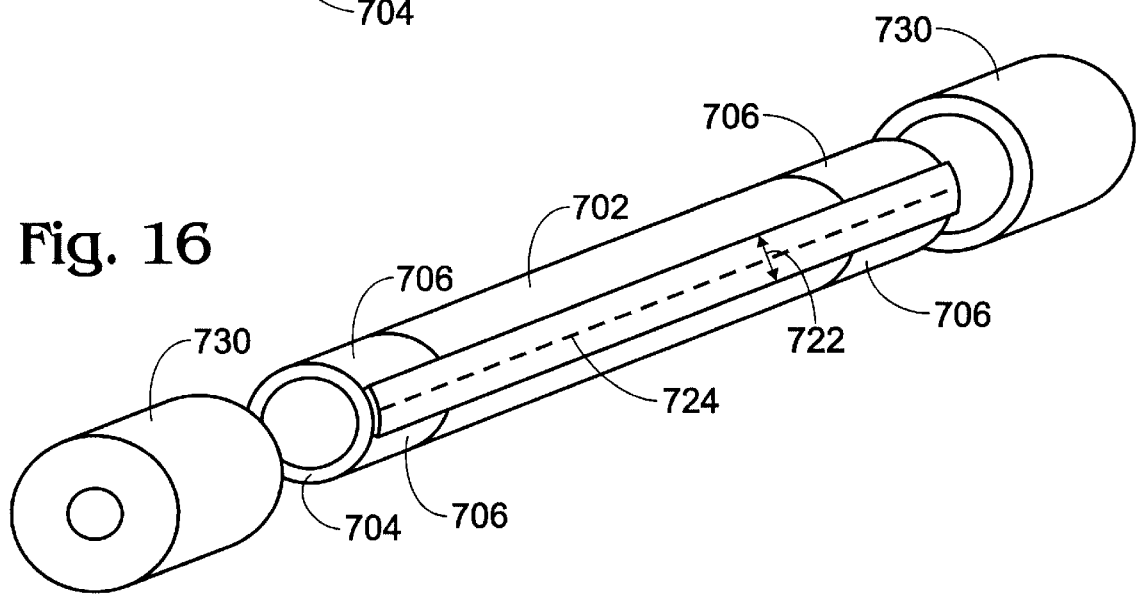

FIGS. 12–16 show the components and manufacturing steps used in constructing a membrane module, e.g., such as illustrated in FIGS. 1, 5, and 6 generally described as a tubular palladium alloy structure supported with end caps. FIGS. 12 and 13 illustrate a palladium alloy foil 702 and a copper or nickel frame 706 joined, respectively, in preparation for joining by ultrasonic welding as illustrated in FIG. 14. FIG. 15 shows the combined palladium alloy foil and copper or nickel frame assembly 720 rolled into a tubular structure and again joined by ultrasonic welding to maintain the tubular structure. In this configuration, the end portion of the tubular assembly bears exposed sections of copper or nickel material. The end caps are then brazed directly to this exposed portion of copper or nickel frame to complete the gas-tight structure.

With reference to FIGS. 12–16, a tubular hydrogen-permeable metal membrane 700 (FIG. 17) was prepared by the following general method of construction. Both Pd-40Cu and Pd-25Ag foil (nominally 25 micron thick) were used as the hydrogen-permeable membrane 702 (shown individually in FIG. 12). A tension spring 704 (FIGS. 15–17), composed of either carbon steel or stainless steel, was used as support within the tubular membrane structure 700.

The first step was to join the palladium-alloy foil 702 to the copper foil frame 706 (nominally 50 microns to 125 microns thick) as shown in FIG. 14. The palladium-alloy foil 702 was typically 8.9 cm wide by 26.4 cm long, and the copper foil frame 706 was typically 10.2 cm wide by 27.9 cm long with a cut out center, equally spaced from all four sides, approximately 7.6 cm wide by 24.1 cm long. This provided a 0.6 cm overlap 710 (FIG. 14) between the palladium-alloy foil 702 and the copper foil frame 706 as foil 702 occupied the cut out center of frame 706.

Ultrasonic welding was used to establish peripheral gas-tight seals 712 between the palladium-alloy foil 702 and the copper foil frame 706 at all four edges of the palladium-alloy foil 702. An Amtech (Shelton, Conn.) Ultraseam Model 40 welder was used. This welder operates at 40 kHz and delivers up to about 750 W of power to the ultrasonic transducer. Both the horn (connected to the ultrasonic transducer) and the anvil rotate at a rate selected by the operator during normal operation of the welder. Welding is accomplished by placing metal between the horn and anvil and applying power to the ultrasonic transducer.

The horn and anvil for the ultrasonic welder are circular, 7.0 cm diameter, with a bearing surface strip about 0.2 cm wide and finished to a surface roughness equivalent to an EDM#3 finish. The horn and anvil were hard coated with titanium nitride. Typical welding parameters are: 40% full power to the transducer, 40 psig applied pressure between the horn and the anvil, 4 rpm rotation rate for the horn and anvil, and the horn "floating" on the foil pieces to be welded (i.e., no preset separation between the horn and anvil). To ensure that the metals are bonded during the welding process, the adjoining metal surfaces should be cleaned of residues such as oxidation, grease and oils, dirt, etc. It is also considered beneficial if the palladium-alloy membrane foil 702 and the copper foil frame 706 are annealed prior to welding, since soft metals are more reliably joined by ultrasonic welding than are hard metals.

After welding the palladium-alloy foil 702 to the copper foil frame 706 to establish the membrane assembly 720 as shown in FIG. 14, the welded seals 712 were examined for leaks by a standard dye penetration test. If no leaks were found, membrane assembly 720 was cleaned of excess dye and then wrapped, as illustrated in FIG. 15, lengthwise around a 2.8 cm (outside diameter) tension spring 704, 27.9 cm long and made from either stainless steel or carbon steel wire nominally 0.25 cm diameter. The overlap 722 of opposite edges of assembly 720 was then joined by ultrasonic welding to form lap seal 724 along the length of the now tubular structure. Lap seal 724 was established by using the ultrasonic welding parameters specified above. Lap seal 724 was then folded over against the membrane tube to conform to a cylindrical shape. Copper end caps 730 (FIG. 16) were then fitted to the membrane tube ends and brazed in place at joints 731 (FIG. 17) using standard copper/phosphorous or copper/silver/phosphorous brazing alloys and a hydrogen/air or hydrocarbon/air (e.g., methane, propane, or acetylene) torch. The brazing alloy is applied only to copper end caps 730 and copper foil frame 706. Important to note, establishing braze joints 731 coupling end caps 730 to the cylindrical form of assembly 720 does not expose the delicate palladium alloy membrane foil 702 to liquid phase material, i.e., does not destroy the delicate, thin foil 702. Because the various ultrasonic welds 712 and 724 establish a gas-tight seal and the braze joints 731 also establish a gas-tight seal, hydrogen passes from a reformation process external of tube 700 only through foil 702. At least one end cap 730 was fitted with a port 732 and outlet 734 to collect the permeate hydrogen from the inside, or bore, of the membrane tube. Within tube 700, a methanation catalyst 740 may be employed whereby purified hydrogen may be taken from membrane tube 700 as described hereinabove. Thus, membranes 700 so constructed are suitable for the high pressure feed gas to be passed over the external surface of the membrane tube, with the permeate collected at the interior surface of the membrane.

Figure 18:
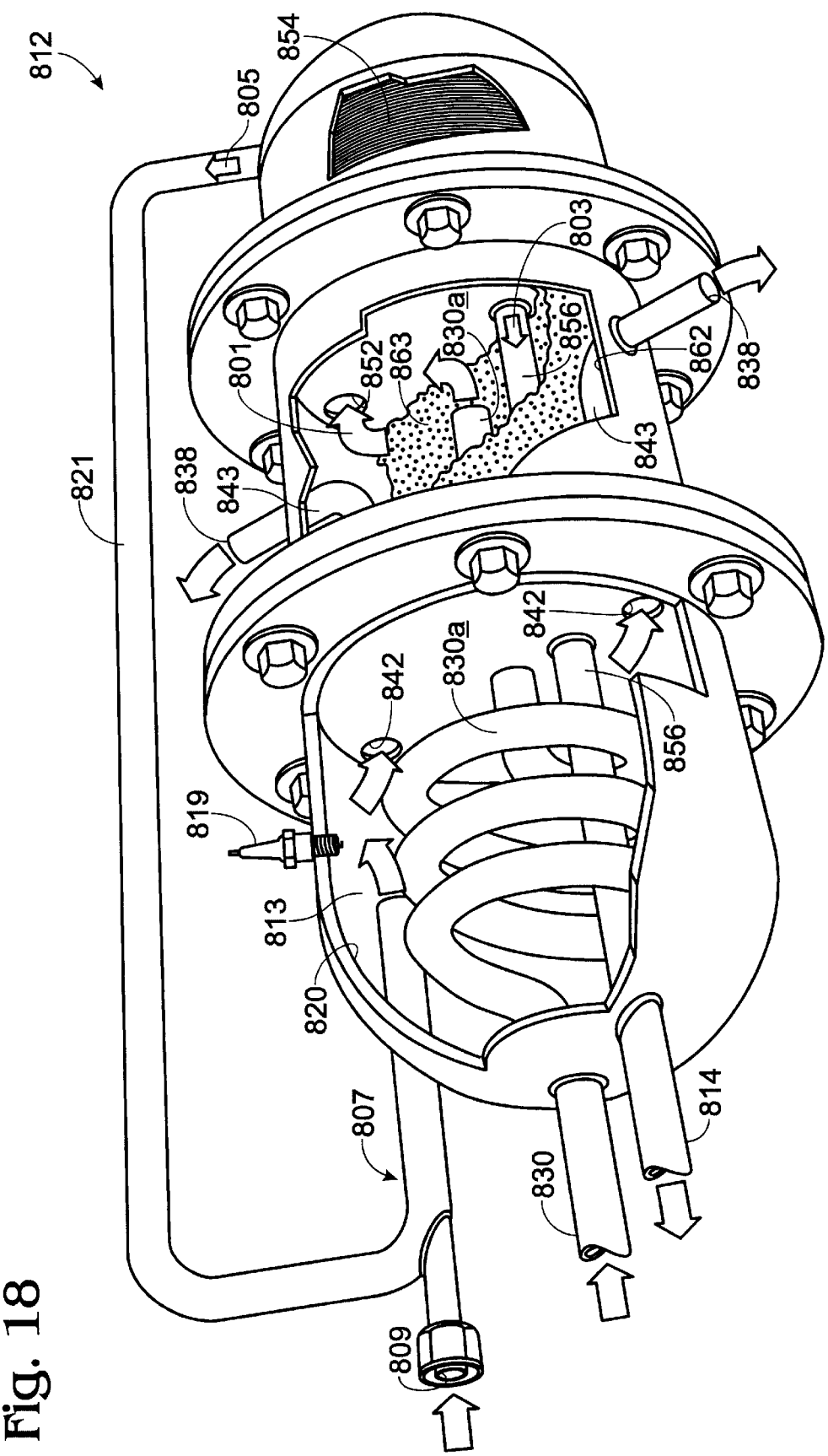
FIG. 18 illustrates in perspective, and partially broken away, another embodiment of a steam reformer according to the present invention including an isolated vaporization chamber and a plate-form membrane module.

FIG. 18 illustrates in perspective and partially broken away, a steam reformer 812 according to another embodiment of the present invention. Reformer 812 employs an isolated vaporization chamber 820 similar to that of reformer 312 (FIG. 6). More particularly, reformer 812 receives at input conduit 830 a feed stock and conduit 830 delivers this mixture into vaporization chamber 820 at the vaporization coil 830a. Elevated temperatures within chamber 820 vaporize the feed stock provided at input conduit 830. Coil 830a passes into and opens into reformation chamber 862. Vaporized fuel thereby enters the reformation chamber 862. Chamber 862 is filled with a reformation catalyst 863 and steam reformation occurs within steam reformation region 862. A reformation product stream 801 exits reformation region 862 at the outlet conduit 852. Conduit 852 delivers product stream 801 to membrane module 854. Module 854 separates stream 801 into a byproduct stream 805 and a hydrogen-rich stream 803.

The hydrogen-depleted reformate byproduct stream 805 travels along conduit 821 from membrane module 854 to a pressure let down valve 823 and then to a manifold 807. Manifold 807 operates in similar fashion to manifold 207 of reformer 212 (FIG. 5). More particularly, manifold 807 introduces an air supply taken from inlet 809, e.g., from a forced air supply, and intermixes it with stream 805 at a mixing region 813. An igniter 819 ignites the intermixed air and stream 805 and the resulting combustion elevates temperatures within the vaporization chamber 820. As in earlier described embodiments of the present invention, stream 805 includes by design a certain amount of hydrogen not taken across the palladium alloy membranes of module 854. Stream 805 thereby serves as a fuel source for combustion within vaporization chamber 820.

Exhaust ports 842 carry the combustion byproducts from chamber 820 through combustion conduits 843 and out exhaust ports 838, shown more clearly in FIG. 19. Conduits 843, however, pass through the reformation chamber 842 and thereby distribute heat throughout reformation region 862 in support of the reformation process therein. Exhaust conduits 843 may take a variety of forms, including finned tubes and spirals, to provide substantial surface area and desirable uniform distribution of heat throughout reformation region 862.

Still referring to FIG. 19, product stream 803 emerging from membrane module 854 travels through a conduit 856 having therein a methanation catalyst 804. Conduit 856 passes through the reformation region 862 and through the vaporization chamber 820 and thereby collects heat energy therefrom in support of the methanation process occurring in conduit 856. The distal end 814 of conduit 856 provides a product outlet, i.e., provides hydrogen in sufficiently purified form for application to, for example, PEM fuel cell 16 (FIG. 1).

FIGS. 20 and 21 illustrate a membrane frame and permeate frame, respectively, employed in the membrane module 854 of FIGS. 18 and 19. In FIG. 20, the membrane frame 870 includes a circular copper or nickel frame 870a with a rectangular center cut out 870b. A rectangular palladium alloy membrane 870c, oversized relative to center cut out 870b, is joined at seals 870d to the frame 870a. By using ultrasonic welding to establish seals 870d about the periphery of palladium alloy membrane 870c, a gas-tight seal results between membrane 870c and frame 870a. Finally, membrane frame 870 includes a feed manifold aperture 872 and a permeate manifold aperture 874.

In FIG. 21, a permeate frame 876 includes a central cut out 876a. Cut out 876a includes a first portion generally rectangular and corresponding generally in dimension to membrane 870c. This portion of cut out 876a is occupied by a wire mesh spacer 876*b*. Other materials that may be used in place of wire mesh spacer 876*b* include porous and foamed ceramic, porous and foamed carbon, and porous and foamed metal. A second portion of cut out 876*a* extends peripherally outward to define a permeate manifold 884 and containing therein a wire mesh insert 876*c*. Frame 876 may be recessed to accommodate face-to-face contact with frame 870, i.e., to accommodate membrane 870*c* as attached to the face of frame 870*b*. Finally, permeate frame 876 includes a feed manifold aperture 882.

As may be appreciated, frame 870 and frame 876 correspond in outer dimensions and certain portions align when stacked. For example, feed manifold 872 aligns with feed manifold 882. Also, permeate manifold 874 may be aligned with the substantially larger permeate manifold 884. Thus, when appropriately stacked with other components, described more fully hereafter, a membrane module 854 may be established to separate stream 801 into streams 803 and 805 as described herein-above.

FIG. 22 illustrates use of frames 870 and 876 stacked to form a series flow arrangement for module 854. In FIG. 22, permeate frame 876 occupies a central position with a membrane frame 870 on each side, i.e., above and below as illustrated in FIG. 22. Feed manifold 882 of frame 876 aligns with feed manifolds 872 of frames 870. Permeate manifold 884 of frame 876 aligns with permeate manifolds 874 of frames 870. Feed frames 880 are located at the outward side of each of frames 870, i.e., above and below frames 870 as illustrated in FIG. 22. Each frame 880 is of circular shape corresponding to that of frames 870 and 876. Each frame 880 includes an open central region extending laterally outward to correspond with, i.e., to fluidly couple with, aligned apertures 872 and 882 of frames 870 and 876. Each frame 880 also includes a permeate manifold aperture 887 isolated relative to the center cut out portion.

Thus, the arrangement illustrated in FIG. 22 offers a series flow configuration directing the feed gas sequentially across successive membranes 870*c*. For example, consider a feed gas traveling upward through the component stack illustrated in FIG. 22. As the feed gas enters the center open region of the lowest frame 880, hydrogen has opportunity to pass through the membrane 870*c* of the lowest membrane frame 870. As may be appreciated, any such hydrogen which does cross the lowest membrane frame 870 migrates into the open region of permeate frame 876 and can then migrate by way of permeate manifolds 884, 874 and 887 out of the component stack for harvest. The series flow arrangement of FIG. 22 offers a second opportunity for feed gas to pass through a membrane 870*c*. More particularly, feed gas travels from the open center region of the lowest frame 880 into the feed manifold 872 of the lowest frame 870, through the feed manifold 882 of the permeate frame 876, through the feed manifold 872 of the upper frame 870, and into the central open region of the upper most feed frame 880. In this open central region, the feed gas is exposed to a second palladium alloy membrane. More particularly, hydrogen remaining in the feed gas as it enters the open region of the upper frame 880 is exposed to the membrane 870*c* of the upper membrane frame 870. Any such hydrogen crossing this upper membrane 870*c* enters the central open region of permeate frame 876 and may then travel along manifolds 884, 874 and 887 for harvest.

As may be appreciated, additional similar components may be stacked in the arrangement illustrated in FIG. 22 to provide successive opportunity for feed gas exposure to palladium alloy membranes in series fashion. An actual implementation would include end plates and necessary outlet and inlet ports for harvesting hydrogen gas and forcing feed gas into the component stack as described earlier in connection with the plate form membrane module 554.

In such series flow arrangement as illustrated in FIG. 22, the feed gas stream is directed to flow over a first membrane surface, then a second membrane surface, and so on as desired. Such series flow arrangement encourages mixing of the feed gas stream components after passage over each membrane in the membrane module component stack.

FIG. 23 illustrates a second arrangement for membrane module components providing a parallel flow configuration, i.e., where the feed stock stream divides and has one opportunity for exposure to a palladium alloy membrane. In FIG. 23, permeate frames 870' correspond generally to the previously described permeate frames 870, but include also a raffinate manifold 875. Similarly, permeate frame 876' corresponds to the previously described permeate frame 876, but includes also a raffinate manifold 885. Raffinate manifolds 885 and 875 align for fluid communication therebetween when frames 870' and 876' stack as illustrated in FIG. 23.

The arrangement illustrated in FIG. 23 establishes a parallel flow of feed gas across the palladium alloy membranes 870*c*. More particularly, consider a feed gas entering the open central region of the lower feed frame 880. Such feed gas is exposed to the membrane 870*c* of the lower frame 870'. Concurrently, some of the feed gas may divert across the lower membrane 870*c* and then travel along the raffinate channels established by apertures 875 and 885, or along the apertures 872 and 882 and eventually enter the open region of the upper feed frame 880. At this point, the feed gas is exposed to the membrane 870*c* of the upper frame 870'. Accordingly, hydrogen present therein may migrate across membrane 870*c* and into the center open region of permeate frame 876'. Thereafter, such hydrogen would pass along manifolds 884 of frame 876' and 874 of frames 870' and eventually through apertures 887 for harvest. In such parallel flow configuration, all of the feed channels over the membrane surfaces are fed from a common feed supply manifold. This favors low pressure drop for the flowing feed gas stream.

The arrangement of membrane component stacking as illustrated in FIGS. 22 and 23 allows series or parallel, respectively, flow of the feed gas through the membrane module. Because the feed frames 880 are compatible, it is possible to combine series flow and parallel flow stacking arrangements in a single membrane module. More particularly, an arrangement such as illustrated in FIG. 22 may be stacked adjacent to an arrangement as illustrated in FIG. 23. Multiple combinations of such arrangements may be provided in a single membrane module as desired to establish a given first-stage of the hydrogen purifier as illustrated in the present invention.

FIG. 24 illustrates an additional frame component which may be incorporated into a membrane module. In FIG. 24, exhaust frame 890 includes a feed manifold aperture 892, a permeate manifold 894, and a raffinate manifold 895. As may be appreciated, stacking exhaust frame 890 in a membrane module such as illustrated in FIGS. 22 and 23 allows passage of feed gas through aperture 892, hydrogen product through aperture 894, and passage of raffinate through aperture 895 without otherwise affecting operation of the membrane modules as described herein above. Exhaust frame 890 includes also an exhaust manifold 897 providing a lateral passage for hot combustion exhaust gas through frame 890. As may be appreciated, exhaust manifold 897 is isolated relative to apertures 892, 894, and 895. Hot exhaust gas passing through exhaust frame 890 elevates the temperature of a membrane module including frame 890 and thereby speeds heating of the membrane module during start up. Exhaust frame 890 may be incorporated into the stacked component structure of a membrane module along with the other frame members by conventional brazing, gasketing, or welding techniques as described herein.

Stacking and construction of the planar-type components as illustrated herein may be executed by use of conventional brazing, gasketing, or welding methods to create a stacked component membrane module. To establish seals between the stacked components of the modules, i.e., the membrane assemblies, permeate and feed frames, exhaust frame members, and end plates, brazing, gasketing, or welding methods are appropriate and may be used without deterioration of the delicate palladium alloy membranes 870c. For example, brazing alloy may be applied between adjoining frame elements and the entire assembly heated to achieve a brazed joint within a controlled-atmosphere brazing furnace. Alternatively, the module may be assembled then welded from the exterior, for example, by using an orbital pipe-welding machine. In yet another proposed method of manufacture of a sealed membrane module, the components are stacked and sufficient pressure applied to the stack such that all joining surfaces are in intimate pressurized contact. Then, heating the entire assembly to between 500 and 800 degrees Celsius for two hours to eight hours results in intermetallic diffusion between the adjoining surfaces to create a sealed joint. Yet another method for achieving gas-tight seals is to use conventional flexible (compressible) graphite gaskets or composite graphite-metal gaskets.

Thus, a variety of embodiments, configurations and alternatives have been shown for implementing steam reformation under the present invention. Various experiments and testing procedures have been conducted to prove the viability of steam reformation under the present invention and will be described in general terms as follows.

As disclosed earlier in the preferred embodiments of the present invention, the hydrogen-rich reformate stream is purified by means of a two-stage hydrogen purifier that is also the subject of this invention. The two-stage hydrogen purifier utilizes a membrane for the first stage to accomplish a bulk separation of hydrogen from the reformate stream. Then, the permeate hydrogen from the first-stage membrane is subjected to a polishing step (the second stage) to further reduce the concentration of selected impurities, such as CO and $CO_2$, to acceptably low levels as required for the hydrogen to serve as the fuel for PEM fuel cells. For instance, a typical PEM fuel cell using a standard platinum electrocatalyst requires hydrogen containing <10 ppm CO and, preferably, <100 ppm $CO_2$ to achieve maximum power output from the fuel cell.

The membrane used in the first stage of the purifier is selected from hydrogen-perneable and hydrogen-selective high-temperature membranes. Thermally-stable membranes allow the purifier to be thermally integrated with the reformer, eliminating the requirement for cooling the hydrogen-rich reformate prior to purification, thereby simplifying the overall system and reducing the cost of the system.

Preferred membranes are microporous ceramic, microporous carbon, microporous metallic, and dense metallic membranes. Especially preferred are thin membranes composed of hydrogen-permeable and hydrogen-selective metals including palladium and palladium alloys, nickel and nickel alloys, and the Group 4 and Group 5 metals and their alloys. Thin membranes composed of Pd-40Cu are especially preferred for high hydrogen permeability and durability. In particular, the Pd-40Cu alloy exhibits highest hydrogen permeability and, therefore, most favorable economics, if the Pd-40Cu alloy contains low concentrations of carbon and oxygen. The following table demonstrates the correlation between high hydrogen permeability (represented as hydrogen flux through the 25 micron thick membrane at 100 psig hydrogen, 400 degrees Celsius) and low carbon content.

| Hydrogen Flux std. $ft^3$-/$ft^2$- · hr | Concentration, ppm | | |
|---|---|---|---|
| | Carbon | Oxygen | Silicon |
| 130 | 40 | 25 | 10 |
| 125 | 56 | 29 | 39 |
| 115 | 146 | 25 | 15 |
| 56 | 219 | 25 | 27 |

The hydrogen-permeable membrane does not have to exhibit an exceptionally high selectivity for hydrogen over other gases, since the second stage of the hydrogen purifier serves to further reduce the concentration of selected impurities that remain in the permeate hydrogen after passing through the membrane. Selectivity is defined as the ratio of the permeation rate of hydrogen divided by the permeation rate of an impurity. The selectivity for hydrogen exhibited by the membrane is at least 20, and preferably at least 50.

Use of such membranes with relatively low selectivity will not yield a permeate hydrogen stream that is of acceptable purity for use in a PEM fuel cell. For example, steam reforming methanol yields a hydrogen-rich reformate stream containing about 25% combined CO and $CO_2$. A membrane with a hydrogen selectivity of 50 will produce a permeate hydrogen stream containing 25%/50=0.5% combined CO and $CO_2$. However, this level of impurities is readily treated with the polishing step (the second stage). Thus, the two-stage hydrogen purifier allows the use of membranes that, due to imperfections or otherwise, have relatively low selectivity for hydrogen over other gases. Such membranes are much less expensive than are membranes that have substantially higher hydrogen selectivity (e.g., hydrogen selectivity >1000).

To obtain a very thin metal hydrogen-permeable membrane without sacrificing mechanical strength of the membrane, the thin hydrogen-permeable membrane is supported by a support layer. The support layer must be thermally and chemically stable under the operating condition of the membrane, and the support layer is preferably porous or containing sufficient voids to allow hydrogen that permeates the thin membrane to pass substantially unimpeded through the support layer. Examples of support layer materials include metal, carbon, and ceramic foam, porous and microporous ceramics, porous and microporous metals, metal mesh, perforated metal, and slotted metal. Especially preferred support layers are woven metal mesh (also known as screen) and tubular metal tension springs.

In the event that the membrane is a thin hydrogen-permeable metal (e.g., palladium alloys) and the support layer is composed of a metal, the metal used for the support layer is preferably selected from a corrosion-resistant alloy, such as stainless steels and non-ferrous corrosion-resistant alloys comprised of one or more of the following metals: chromium, nickel, titanium, niobium, vanadium, zirconium, tantalum, molybdenum, tungsten, silicon, and aluminum. These corrosion-resistant alloys have a native surface oxide layer that is chemically and physically very stable and serves to significantly retard the rate of intermetallic diffusion between the thin metal membrane and the metal support layer. Such intermetallic diffusion, if it were to occur, often results in significant degradation of the hydrogen permeability of the membrane and is undesirable [see Edlund, D. J., and J. McCarthy, "The Relationship Between Intermetallic Diffusion and Flux Decline in Composite-Metal Membranes: Implications for Achieving Long Membrane Lifetimes" *J Membrane.*, 107 (1995)147–153].

The rate of intermetallic diffusion between the thin metal membrane and the metal support layer may also be retarded by applying certain non-porous coatings to the metal support. Suitable coating materials include aluminum oxide; aluminum nitride; silicon oxide; tungsten carbide; tungsten nitride; oxides, nitrides, and carbides of the Group 4 and Group 5 metals; boron nitride; and boron carbide. Many of these coating are employed as hard coatings on tools and dies, and as release agents.

The second stage of the hydrogen purifier is designed to further reduce the concentration of impurities that adversely affect the power output and operation of the PEM fuel cell. Particularly, the second-stage polishing step is designed to remove CO and, to a lesser degree, $CO_2$ from the hydrogen that has permeated the first-stage membrane. Furthermore, the second-stage polishing step is conducted at or near the operating temperature of the first-stage membrane and the reformer, thereby eliminating the need to substantially heat or cool the hydrogen stream before passage through the polishing step. By thermally integrating the polishing step, the need for heat exchangers is eliminated and the overall operation of the system is simplified and the cost of the system is reduced.

Suitable chemical operations for the second-stage polishing step include preferential oxidation of CO, a widely practiced method for removing CO from hydrogen fuel streams for PEM fuel cells [Swathirajan, S., and H. Fronk, "Proton-Exchange-Membrane Fuel Cell for Transportation" *Proceedings of the Fuel Cells '94 Contractors Review Meeting*, DOE/METC-94/1010, Aug. 17–19 (1994) 105–108]. However, selective oxidation only removes CO from the hydrogen stream, it does not reduce the $CO_2$ content. In fact, selective oxidation increases the $CO_2$ content of the hydrogen. A preferred chemical operation for the polishing step is methanation, which removes both CO and $CO_2$ from the hydrogen stream, as represented by the following chemical reactions:

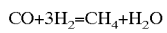

$CO + 3H_2 = CH_4 + H_2O$

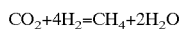

$CO_2 + 4H_2 = CH_4 + 2H_2O$

Methanation occurs rapidly at >300° C. in the presence of a catalyst, such as nickel, palladium, ruthenium, rhodium, and platinum. Preferably, methanation is conducted at 400° C. to 600° C. in the presence of a commercial supported nickel reforming or methanation catalyst such as R1-10 and G1-80 manufactured and sold by BASF.

As the embodiments described earlier have shown, the first stage and second stage of the hydrogen purifier can be integrated so that they are in close proximity, thereby minimizing heat loss as well as reducing the size, weight, and cost of the hydrogen purifier. For example, if a tubular membrane is used as the first stage, the second-stage polishing step may be located within the bore of the membrane tube at the permeate side of the membrane. If a plate-type membrane is selected, the polishing step may be located at the permeate side of the membrane between membrane plates, or it may be located in a tube or other shape that is directly connected to the plate-type membrane at the permeate-hydrogen discharge port. Furthermore, if the membrane is supported for strength, and if the polishing step is methanation, the methanation catalyst may be incorporated within the support for the membrane. For instance, the membrane support may comprise a nickel or other metal mesh with a high nickel surface area.

While previously disclosed embodiments of the invention have shown the two-stage hydrogen purifier as an integral part of the fuel processor, it will be appreciated that the two-stage hydrogen purifier may function external to a conventional process for hydrogen manufacture (e.g., steam reformer, partial-oxidation reactor, or autothermal reformer).

Concerns over safety call for use of non-flammable fuel feedstocks for use to produce hydrogen by the steam-reforming process. The advantages of using non-flammable fuel feedstocks include elimination of fire or explosion danger due to vapors from the fuel feedstock accumulating in enclosed environments and, for military applications, elimination of fire or explosion risk from hot metal fragments striking and penetrating fuel storage tanks.

Non-flammable fuel feedstocks for generating hydrogen by steam reforming and as disclosed in this invention include polyhydroxy alcohols and polyethers that are miscible with water. As used herein, non-flammable means that combustion in normal air at about 1 atm. pressure is not self-sustaining. Preferred fuels include ethylene glycol, propylene glycol, and the glycol ethers of ethylene glycol and propylene glycol (e.g., diethylene glycol). These fuels are collectively called glycols. When mixed with a stoichiometric amount of water for steam reforming (e.g., two molar equivalents water to one molar equivalent ethylene glycol; and four molar equivalents water to one molar equivalent propylene glycol), these fuel feedstocks are not flammable even when subjected to a propane/air flame from a torch. The flame merely heats the glycol/water mixture until the water in the mixture boils. Provided substantial water is still present in the glycol/water mixture, combustion is not supported.

The non-flammable nature of the glycol/water mixtures is due to the very low vapor pressure of the glycol component (e.g., ethylene glycol and propylene glycol). For instance, the vapor pressure of ethylene glycol is only 20 torr at 100° C. Furthermore, the water component of these mixtures, in addition to being a necessary reactant for steam reforming, serves two functions that contribute to the non-flammable nature of these glycol/water mixtures. First, water in the mixture serves, by evaporative cooling, to reduce the maximum temperature to which the mixture can be heated thereby limiting the maximum vapor pressure of the glycol. Second, as water evaporates at the surface of the mixture, the water vapor dilutes oxygen (from air) at the surface of the glycol/water mixture. Since oxygen is necessary for combustion, and combustion is generally favored by high oxygen concentrations, substantial dilution of oxygen from air by evaporating water serves to reduce the flammability of the glycol/water mixture.

Thus, certain feedstock mixtures are non-flammable. Simply stated, to be non-flammable the vapor pressure of the combustible component, i.e., organic component, of the fuel feedstock must remain below the lower flammability limit at 100° C.; the approximate temperature at which water in the mixture will boil. Generally, this requires that the organic component have a vapor pressure <100 torr at 100° C.

In addition to being non-flammable, glycol/water mixtures, best known for their use as heat exchange fluids in internal combustion engines, are converted to a hydrogen-rich reformate stream in the presence of nickel-based steam-reforming catalysts at temperatures in the range of 400° C. to 700° C. Glycol/water mixtures also offer the advantage of forming stable solutions over a wide range of water concentration, so that the proper water to glycol steam reforming ratio can be obtained by appropriately mixing the glycol/water fuel feedstock and then dispensing this fuel feedstock into a supply tank (or reservoir) from which the fuel feedstock is delivered at the proper rate to the reformer. Yet another advantage of the glycol/water mixtures is that they remain liquid over a large temperature range, and they are generally viscous liquids. Glycol/water mixtures, sold commercially as antifreeze coolants, remain liquid even at temperatures well below 0° C. and at temperatures greater than 100° C. Being liquid, glycol/water mixtures are efficiently pumped to elevated pressure for delivery to the reformer so that steam reforming can be conducted at elevated pressure (up to 500 psig, but preferably 100 psig to 300 psig). The high viscosity of glycol/water mixtures leads to greater pumping efficiency, particularly if a gear pump, piston pump, or centrifugal pump is used to deliver the high-pressure fuel feedstock to the reformer. The high viscosity reduces slippage past the wetted surfaces of the pump, which often limits the maximum pressure differential at which a pump may be used.

To demonstrate the integrated fuel processor of this invention, the fuel processor depicted generally in FIG. 5 was constructed and operated. The tubular metal membrane (first stage of the hydrogen purifier) was made using the method generally described in connection with FIGS. 12–17. The hydrogen-permeable metal foil 702 consisted of Pd-40Cu nominally 25 microns thick, and the membrane was about 15 cm long (2.8 cm outside diameter). The second stage of the hydrogen purifier, a catalytic methanizer, was contained in a copper tube, 1.8 cm outside diameter, that was inserted inside the bore of the tubular membrane 700. One end of the copper methanation tube was sealed to one of the tubular-membrane end caps 730. The other end of the copper methanation tube was terminated about 0.3 cm from the end of the membrane tube whereby hydrogen permeating to the inside of the membrane tube 700 would freely flow into the open end of the methanation tube such as shown generally in FIG. 3. The methanation tube was filled with catalyst G1-80 (BASF), a supported nickel composition that is active for methanation of CO and $CO_2$.

The reforming region of the fuel processor was filled with catalyst K3-110, a copper/zinc supported catalyst sold by BASF generally for conducting the water-gas shift reaction at <350° C. The shell of the fuel processor, the spiral combustion tube, and the end plates were all constructed from stainless steel. Insulation was placed around the exterior of the shell and end plates to reduce heat loss.

The fuel processor was operated using methanol/water mix as the feed. The methanol/water solution was prepared by mixing 405 mL methanol (histological grade, Fisher Scientific) with 180 mL deionized water. The fuel processor was heated to 200° C. to 300° C. using an externally placed electric resistance heater. Once the fuel processor was hot, the electric heaters were turned off and methanol/water solution was pumped into the fuel processor at 200 psig. The methanol/water feed was first vaporized then the vapors passed over the K3-110 reforming catalyst to produce hydrogen-rich reformate. The two-stage hydrogen purifier then extracted product hydrogen at ambient pressure from the hydrogen-rich reformate. The hydrogen-depleted raffinate was directed to the combustor as described above. Combustion of this raffinate gas inside the fuel processor heated the fuel processor to 300° C. to 350° C. and provided all required heat once operation of the fuel processor commenced.

The purity of the product hydrogen was determined by gas chromatography and the flow rate of the product hydrogen was measured using a calibrated gas flow meter. Analysis of the product hydrogen confirmed <10 ppm CO and <10 ppm $CO_2$. The flow rate of product hydrogen was 2 L/min. The reformer was operated in this mode, without any external source of heating, for 6 hours at which time the experiment was concluded.

Figure 17:
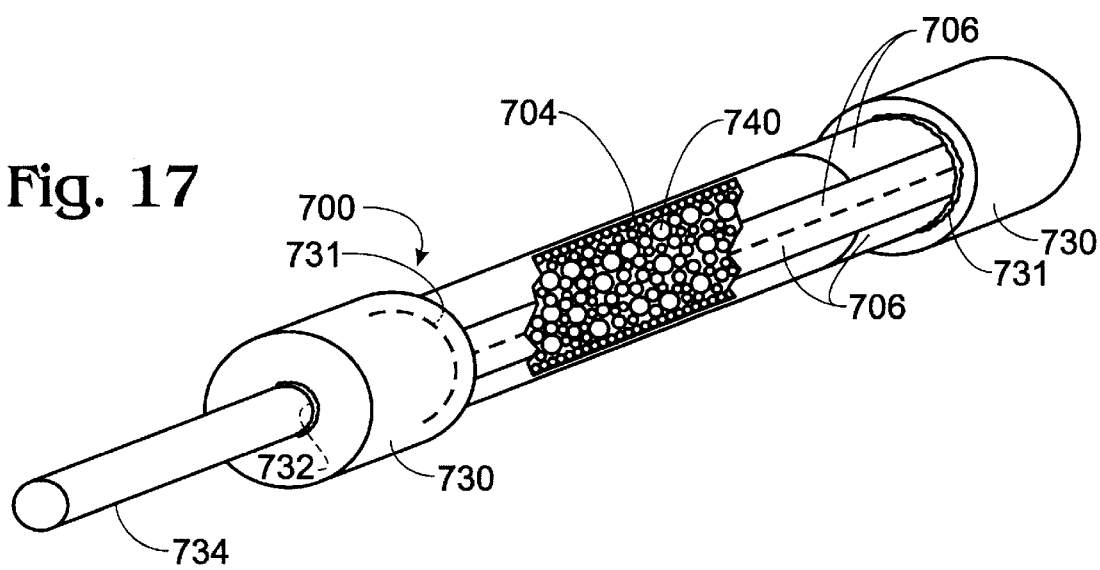

According to a second example, tubular Pd-25Ag membranes with a 2.2 cm outside diameter were made using the general method described in connection with FIGS. 17–17. The Pd-25Ag foil was 25 micron thick and 7.0 cm wide by 16 cm long and the copper foil frame was 125 micron thick and 8.3 cm wide by 17.8 cm long. The dimensions of the center cut out in the copper foil frame was 5.7 cm wide by 14 cm long. The welding equipment and methods described in connection with FIGS. 12–17 were used to join the palladium-alloy foil to the copper foil frame. The support for the membrane was a carbon steel tension spring, 2.2 cm outside diameter. The spring was made using wire nominally 0.25 cm diameter. End caps were brazed to the ends of the membrane tube using the method given above or, in some cases, end caps were sealed to the ends of the membrane tube using graphite seals. The graphite seals were achieved using flexible graphite tape (1.3 cm wide) wrapped around the membrane tube and then compressed against the membrane in a standard compression fitting.

In another example, plate-type membrane modules were made using the following general method. Hydrogen-permeable Pd-40Cu foil, nominally 25 micron thick and 5.1 cm by 5.1 cm square, were welded to a copper foil frame (nominally 125 micron thick) using the ultrasonic welder and welding parameters discussed above. The copper foil frame was circular in shape (8.9 cm diameter) with cut outs for feed and permeate as shown in FIG. 20. After welding the Pd-40Cu membrane to the copper foil frame to make the membrane assembly, the weld was checked for leaks by a standard dye penetration test.

The copper permeate plate (FIG. 21) was 0.3 cm thick and 8.9 cm diameter. A recessed was machined in the permeate plate to accept the support layer for the membrane. This recess, as shown in FIG. 21, was of the same dimensions as the membrane and connected to the permeate manifold channel. The support layer consisted of a first layer of stainless steel screen (70×70 mesh), placed against the permeate plate, then a second layer of stainless steel screen (200×200 mesh) that the thin Pd-40Cu foil rested against. This combination of coarse mesh and fine mesh was determined to both adequately support the thin membrane without excessively damaging the membrane, and provide acceptably low resistance to the lateral flow of permeate hydrogen.

The stainless steel screen was fixed to the permeate plate with a single drop of cyanoacrylate glue, and the glue allowed to dry. Then, two membrane assemblies were brazed to a single permeate plate, one membrane assembly at each major surface of the permeate plate. Brazing was achieved using a standard brazing alloy (nominally 80% copper, 15% silver, and 5% phosphorous) in either ribbon form or as a paste (powdered brazing alloy mixed with a paste binder). This brazing alloy was purchased from Lucas-Milhaupt, Inc. (Cudahy, Wisc.). To prevent unwanted creep of the brazing alloy over the surface of the Pd-40Cu membrane, Nicrobraz Red Stop-Off Type II (Wall Colmonoy Corp., Madison Hts., Mich.) was applied around the edge of the Pd-40Cu membrane. This assembly was then placed on a flat surface beneath a steel weight (approximately 1.5 kg) and heated to 750° C. in a brazing furnace. A coating of boron nitride, a release agent, was applied to the steel surfaces in contact with the membrane assembly during brazing to prevent sticking between the membrane assembly and the steel surfaces. Brazing was done under vacuum, a nitrogen atmosphere, or a nitrogen stream containing a low concentration of methanol or hydrogen to serve as a reducing gas (to prevent oxidation). The brazing temperature of 750° C. was held for 15 minutes prior to cooling.

To demonstrate the non-flammability of ethylene glycol/water mixtures, the following experiment was conducted. Ethylene glycol (1.0 mL) was mixed with two molar equivalents water (0.65 mL). The resulting homogeneous solution is of the proper stoichiometry for steam reforming, as shown by the following ideal reaction equation:

$$HOCH_2CH_2OH + 2H_2O = 2\ CO_2 + 5H_2$$

This solution of ethylene glycol and water was directly exposed to the flame from a propane/air torch. The ethylene glycol/water solution did not bur or support combustion.

In yet another example, a 2:1 molar ratio of water-to-ethylene glycol was prepared by mixing 65 mL deionized water and 100 mL purified reagent grade (Fisher Scientific) to form a homogeneous solution. This ethylene glycol/water solution was reformed to produce hydrogen in a laboratory-scale packed-bed catalytic reactor as described below.

The catalytic reactor consisted of a cylindrical stainless steel shell 2.5 cm inside diameter and 22.9 cm long. The reactor contained a fixed bed of the commercial catalyst G1-80 (BASF), which is a supported nickel steam reforming catalyst. A length of stainless steel tubing (0.3 cm diameter by about 25 cm long) was coiled around one end of the catalytic reactor to serve as a preheater and vaporizer for the ethylene glycol/water feed. One end of this vaporization coil was connected to the inlet of the catalytic reactor, the other end of the coil was connected to a reservoir containing the ethylene glycol/water feed. The temperature within the catalytic reactor was measured and controlled via a thermocouple inserted within the catalyst bed.

The catalytic reactor was heated to 500° C. by means of an external electric furnace. The G1-80 catalyst was then reduced in situ by first flowing ethylene glycol/water feed into the catalytic reactor at a rate of 2.5 mL/min (liquid flow rate) for 2 hrs, then flowing pure hydrogen at ambient pressure through the catalytic reactor for another 4 hrs. Following reduction of the steam reforming catalyst, ethylene glycol/water feed was admitted into the catalytic reactor at ambient pressure. The temperature of the catalytic reactor was varied between 400° C. and 500° C. The product gas was shown to be predominantly $CO_2$ and $H_2$ by gas chromatography analysis, unreacted ethylene glycol/water was collected in a cold trap and quantified by gravimetric analysis, and the product flow rate was measured using a calibrated gas flow meter to determine the degree of conversion to products. The results of these experiments are summarized in the following table.

| Temperature (° C.) | Product Flow Rate (L/min) | Conversion to Products (%) |
|---|---|---|
| 500 +/− 50 | 3–5 | 90–95 |
| 465 +/− 25 | 4–5 | 90–95 |
| 400 +/− 25 | 4–5 | 93–98 |

To demonstrate the utility of the two-stage hydrogen purifier when utilized as a stand-alone hydrogen purifier, the following experiment was conducted.

A tubular hydrogen-permeable metal membrane was made using the method described in FIGS. 12–17. The membrane consisted of Pd-25Ag foil nominally 25 micron thick and was 2.2 cm outside diameter by 15 cm long, the overall length of the membrane tube (including end caps) was approximately 21 cm. This tubular membrane serves as the first stage of the purifier. The second stage of the purifier, a catalytic methanizer, was contained in a copper tube, 1.58 cm outside diameter, that was inserted inside the bore of the tubular membrane. One end of the copper methanation tube was sealed to one of the tubular-membrane end caps. The other end of the copper methanation tube was terminated about 0.3 cm from the end of the membrane tube so that hydrogen permeating to the inside of the membrane tube would freely flow into the open end of the methanation tube (this arrangement is shown in FIG. 3). The methanation tube was filled with catalyst G1-80 (BASF), a supported nickel composition that is active for methanation of CO and $CO_2$.

This two-stage hydrogen purifier was placed in a stainless steel shell equipped with electric resistance heaters. The hydrogen purifier was heated to 300° C. to 350° C., and methanol/water reformate (approximately 70–75% hydrogen, balance CO and $CO_2$) at 50 psig was passed into the stainless steel shell and over the exterior surface of the Pd-25Ag membrane tube. Product hydrogen at ambient pressure, after permeation through the Pd-25Ag membrane and then passage over the methanation catalyst, was collected and analyzed by gas chromatography. Analysis confirmed that the product hydrogen contained <2 ppm CO and <50 ppm $CO_2$.

Thus, a steam reformer with internal hydrogen purification has been shown and described. The reformer of the present invention utilizes a single feed, e.g., a methanol and water or hydrocarbon and water mix, as both the chemical feed stock to support hydrogen reforming and also as a combustion fuel source to provide sufficient temperature to support steam reforming. The present invention recovers by design less than a maximum amount of hydrogen available in a reforming step to leave in the byproduct stream sufficient hydrogen as fuel to support the combustion process. The present invention uses two distinct hydrogen purification processes. First, a membrane produces a hydrogen stream as a bulk filtration step, but the product hydrogen stream may still contain some undesirable impurities. Second, a polishing process converts the undesirable impurities in the hydrogen stream to innocuous components not affecting operation of, for example, a fuel cell. Advantageously, this allows use of a relatively less expensive, thin palladium-alloy membrane in the steam reforming process.

It will be appreciated that the present invention is not restricted to the particular embodiment that has been described and illustrated, and that variations may be made therein without departing from the scope of the invention as found in the appended claims and equivalents thereof.

What is claimed is:

1. A steam reformer, comprising:
a reformation chamber containing a reformation catalyst, wherein the reformation chamber is adapted to receive a reformation feedstock and produce a reformate stream including hydrogen therefrom; and
a membrane module adapted to receive the reformate stream and divide the reformate stream into a byproduct stream and a hydrogen product stream, the membrane module comprising:
a plurality of hydrogen permeable membranes, each having a reformate side and a permeate side, wherein the membranes are spaced-apart from each other and oriented with their permeate sides generally facing each other to define a harvesting conduit extending therebetween, and further wherein the hydrogen product stream is formed from the portion of the reformate stream that passes through the membranes to the harvesting conduit, with the remaining portion of the reformate stream which remains on the reformate side of the membranes forming the byproduct stream;
a support within the harvesting conduit adapted to support the membranes, wherein the support includes a pair of generally opposed surfaces which are adapted to provide support to a respective one of the permeate sides of the membranes; and
a product outlet port in fluid communication with the harvesting conduit and through which the hydrogen product stream is withdrawn from the membrane module.

2. The reformer of claim 1, wherein the support engages but is not bonded to the membranes.

3. The reformer of claim 1, wherein the support is formed from a porous material.

4. The reformer of claim 1, wherein the support is adapted to permit flow of gas both parallel and transverse to the permeate sides of the membranes.

5. The reformer of claim 1, wherein the support defines a gas stream path through the harvesting conduit, with the stream path extending parallel and transverse to the permeate sides of the membranes.

6. The reformer of claim 1, wherein the support includes mesh.

7. The reformer of claim 6, wherein the support includes an inner mesh screen with outer mesh screens separating the inner mesh screen and the permeate sides of the membranes.

8. The reformer of claim 7, wherein the inner mesh screen is coarser than the outer mesh screens.

9. The reformer of claim 1, wherein the membranes define generally parallel, spaced-apart planes with the harvesting conduit extending therebetween and being at least substantially coextensive therewith.

10. The reformer of claim 1, wherein each membrane includes an edge region secured to a frame that extends beyond the edge region of the membrane.

11. The reformer of claim 10, wherein the frame is bonded to the edge region by ultrasonic welding.

12. The reformer of claim 10, wherein the reformer includes a plurality of gas transport conduits extending through the frames to selectively deliver the reformate stream to the reformate sides of the membranes, remove the product stream from the harvesting conduit, and to remove the byproduct stream.

13. The reformer of claim 12, wherein at least one of the conduits is adapted to deliver the byproduct stream to a combustion region of the reformer.

14. The reformer of claim 12, wherein at least one of the conduits is adapted to deliver the product stream to a polishing catalyst bed.

15. The reformer of claim 1, wherein the support and the membranes whose permeate sides are supported by the support comprise a membrane envelope, and further wherein the membrane module includes plural membrane envelopes.

16. The reformer of claim 15, wherein each membrane envelope includes an inlet port through which at least a portion of the reformate stream is delivered to the membrane envelope, a product outlet port through which the product stream is withdrawn from the harvesting conduit, and a byproduct port through which the byproduct stream is withdrawn from the membrane envelope, and further wherein the corresponding ports of the plurality of membrane envelopes are in fluid communication with each other to respectively form an inlet conduit, a product conduit and a byproduct conduit.

17. The reformer of claim 16, wherein the byproduct conduit is adapted to deliver the byproduct stream to a combustion region of the reformer.

18. The reformer of claim 16, wherein the product conduit is adapted to deliver the product stream to a polishing catalyst bed.

19. The reformer of claim 1, wherein each hydrogen permeable membrane is formed from at least one of palladium or a palladium alloy.

20. The reformer of claim 19, wherein each membrane contains less than 200 ppm carbon.

21. The reformer of claim 20, wherein each membrane contains less than 100 ppm carbon.

22. The reformer of claim 21, wherein each membrane contains less than 50 ppm carbon.

23. A hydrogen-selective membrane envelope, comprising:
a hydrogen permeable membrane region having an inlet side and a permeate side;
another hydrogen permeable membrane region having an inlet side and a permeate side, wherein the membrane regions are spaced-apart from each other with their permeate sides facing each other and defining a harvesting conduit extending therebetween;
a support within the harvesting conduit and adapted to support the permeate sides of the membrane regions, wherein the support enables gas passing through the membrane regions to the harvesting conduit to travel transverse and parallel to the permeate sides of the membrane regions; and
an outlet port through which gas may be harvested from the harvesting conduit.

24. The membrane envelope of claim 23, wherein the envelope is in fluid communication with a steam reformer and adapted to receive a reformate stream containing hydrogen therefrom.

25. The membrane envelope of claim 24, wherein the envelope is coupled to the steam reformer.

26. The membrane envelope of claim 25, wherein the envelope is at least partially contained within the steam reformer.

27. The membrane envelope of claim 23, wherein the support engages the permeate sides of the membrane regions but is not bonded to the permeate sides of the membrane regions.

28. The membrane envelope of claim 23, wherein the support includes mesh.

29. The membrane envelope of claim 28, wherein the support includes an inner mesh screen and outer mesh screens separating the inner mesh screen and the permeate sides of the membrane regions.

30. The membrane envelope of claim 29, wherein the inner mesh screen is coarser than the outer mesh screens.

31. The membrane envelope of claim 23, wherein the membrane regions define generally parallel, spaced-apart surfaces with the harvesting conduit extending therebetween.

32. The membrane envelope of claim 23, wherein each membrane region includes an outer edge region to which a frame is bonded.

33. The membrane envelope of claim 32, wherein each frame is bonded to the outer edge region of a corresponding one of the membrane regions by ultrasonic welding.

34. The membrane envelope of claim 23, wherein each of the membranes is formed from at least one of palladium and a palladium alloy.

35. The membrane envelope of claim 24, wherein each of the membranes contains less than 200 ppm carbon.

36. The membrane envelope of claim 35, wherein each of the membranes contains less than 100 ppm carbon.

37. The membrane envelope of claim 36, wherein each of the membranes contains less than 50 ppm carbon.

* * * * *

UNITED STATES PATENT AND TRADEMARK OFFICE
CERTIFICATE OF CORRECTION

PATENT NO. : 5,997,594
DATED : December 7, 1999
INVENTOR(S) : David J. Edlund and William A. Pledger It is certified that error appears in the above-indentified patent and that said Letters Patent is hereby corrected as shown below:

In column 32, line 7, delete "24" and insert --34-- therefor.

Signed and Sealed this

Fourth Day of July, 2000

Attest:

Q. TODD DICKINSON

*Attesting Officer*  *Director of Patents and Trademarks*